US012665066B2

(12) United States Patent
Marlow et al.

(10) Patent No.: US 12,665,066 B2
(45) Date of Patent: Jun. 23, 2026

(54) DETECTION AND EVALUATION OF A SURGICAL TIME-OUT CONFIRMING SURGICAL DETAILS FROM CAPTURED VIDEO OF AN OPERATING ROOM

(71) Applicant: Apella Technology Inc., Oakland, CA (US)

(72) Inventors: Cameron Alexander Marlow, Menlo Park, CA (US); David Michael Schummers, Oakland, CA (US); Jordan Stuart Tuttle, San Diego, CA (US)

(73) Assignee: Apella Technology Inc., Oakland, CA (US)

( * ) Notice: Subject to any disclaimer, the term of this patent is extended or adjusted under 35 U.S.C. 154(b) by 642 days.

(21) Appl. No.: 17/992,919

(22) Filed: Nov. 22, 2022

(65) Prior Publication Data

US 2024/0170127 A1     May 23, 2024

(51) Int. Cl.
G16H 20/40        (2018.01)
G06N 20/00        (2019.01)
(Continued)

(52) U.S. Cl.
CPC ............. G16H 20/40 (2018.01); G06N 20/00 (2019.01); G06V 20/44 (2022.01); G06V 20/52 (2022.01);
(Continued)

(58) Field of Classification Search
CPC ........ G16H 40/20; G16H 70/20; G16H 20/40; G16H 50/20; G16H 10/60; G16H 40/40;
(Continued)

(56) References Cited

U.S. PATENT DOCUMENTS

| | | | | |
|---|---|---|---|---|
| 9,305,155 B1 * | 4/2016 | Vo | .......................... | G06F 3/0482 |
| 2010/0082368 A1 * | 4/2010 | Gecelter | ................ | G16H 40/20 |
| | | | | 705/3 |

(Continued)

OTHER PUBLICATIONS

Guzmán-García, Carmen, et al. "Speech-based surgical phase recognition for non-intrusive surgical skills' assessment in educational contexts." Sensors 21.4 (2021): 1330. (Year: 2021).*

*Primary Examiner* — Sumati Lefkowitz
*Assistant Examiner* — Ryan P Potts
(74) *Attorney, Agent, or Firm* — Fenwick & West LLP

(57)         ABSTRACT

Multiple image capture devices are located in an operating room to capture video of the entirety of the operating room. A surgical tracking server applies one or more models to the captured video to determine states of objects in the operating room from which a phase of the operating room is determined. A surgical time-out where information about a surgical procedure is audibly provided by people in the operating room during the surgical procedure. From audio and video of the operating room, the surgical tracking server determines whether the time-out was performed and identifies audio and video corresponding to the surgical time-out. The identified audio and video are compared to criteria to evaluate completeness of the surgical time-out. A quality metric for the time out based on the captured video data based on characteristics of the video or audio of the operating room may also be generated.

30 Claims, 6 Drawing Sheets

(51) Int. Cl.

| | |
|---|---|
| *G06V 20/40* | (2022.01) |
| *G06V 20/52* | (2022.01) |
| *G16H 70/20* | (2018.01) |
| *A61B 90/00* | (2016.01) |
| *G16H 40/20* | (2018.01) |

(52) U.S. Cl.

CPC .............. *G16H 70/20* (2018.01); *A61B 90/37* (2016.02); *G06T 2207/10016* (2013.01); *G06T 2210/41* (2013.01); *G16H 40/20* (2018.01)

(58) Field of Classification Search

CPC ........ G16H 40/67; G16H 15/00; G16H 40/63; G16H 50/70; A61B 34/25; A61B 90/37; A61B 2034/252; A61B 2017/00119; A61B 90/361; A61B 2034/254; A61B 2034/2065; A61B 2034/302; A61B 2090/064; A61B 2090/08021; A61B 2090/371; A61B 2503/20; A61B 2505/05; A61B 2560/0219; A61B 34/10; A61B 34/37; A61B 34/74; A61B 5/0013; A61B 5/1128; A61B 5/117; A61B 5/411; A61B 5/4803; A61B 5/749; A61B 90/36; A61B 90/90; G06N 20/00; G06V 20/44; G06V 20/52; G06T 2207/10016; G06T 2210/41

See application file for complete search history.

(56) References Cited

U.S. PATENT DOCUMENTS

| | | | | |
|---|---|---|---|---|
| 2014/0297331 | A1* | 10/2014 | Vazquez | G16H 10/20 |
| | | | | 705/3 |
| 2018/0247024 | A1* | 8/2018 | Divine | G16H 40/20 |
| 2020/0194111 | A1* | 6/2020 | Venkataraman | A61B 90/37 |
| 2020/0350063 | A1* | 11/2020 | Thornton | G06V 20/52 |
| 2021/0338344 | A1* | 11/2021 | Abovitz | A61B 34/20 |
| 2022/0101999 | A1* | 3/2022 | Bonutti | A61N 1/3605 |
| 2023/0402166 | A1* | 12/2023 | Tiwary | A61B 90/361 |

* cited by examiner

100

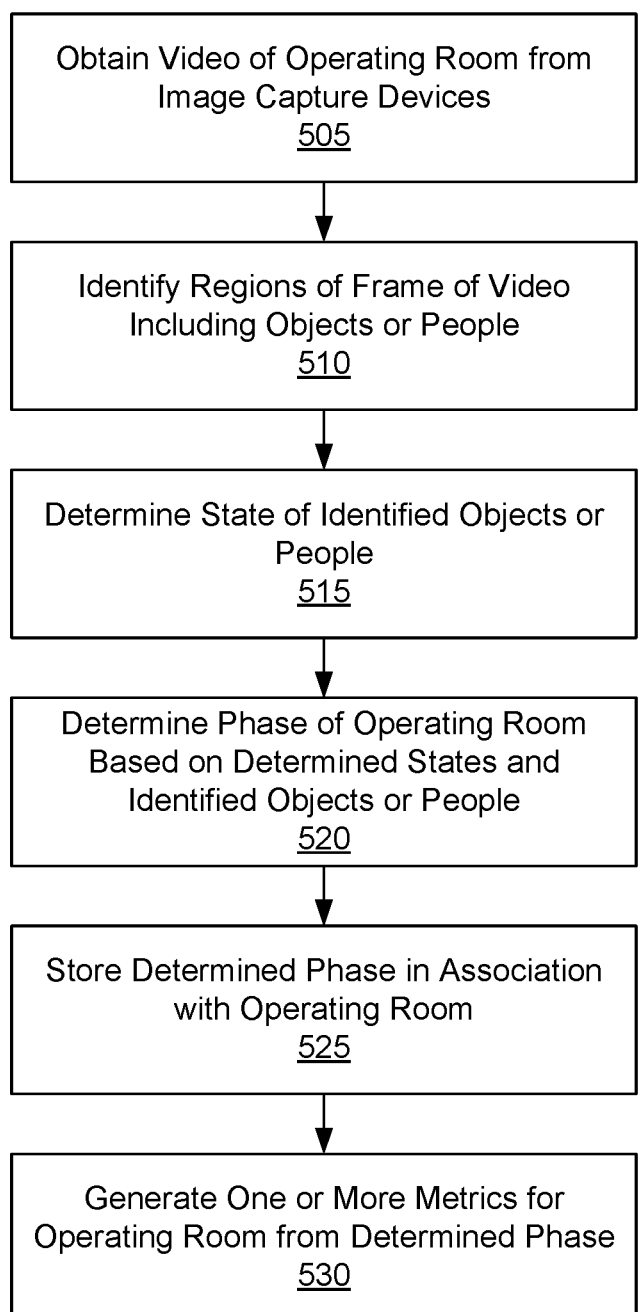

Obtain Video of Operating Room from
Image Capture Devices
505

Identify Regions of Frame of Video
Including Objects or People
510

Determine State of Identified Objects or
People
515

Determine Phase of Operating Room
Based on Determined States and
Identified Objects or People
520

Store Determined Phase in Association
with Operating Room
525

Generate One or More Metrics for
Operating Room from Determined Phase
530

FIG. 5

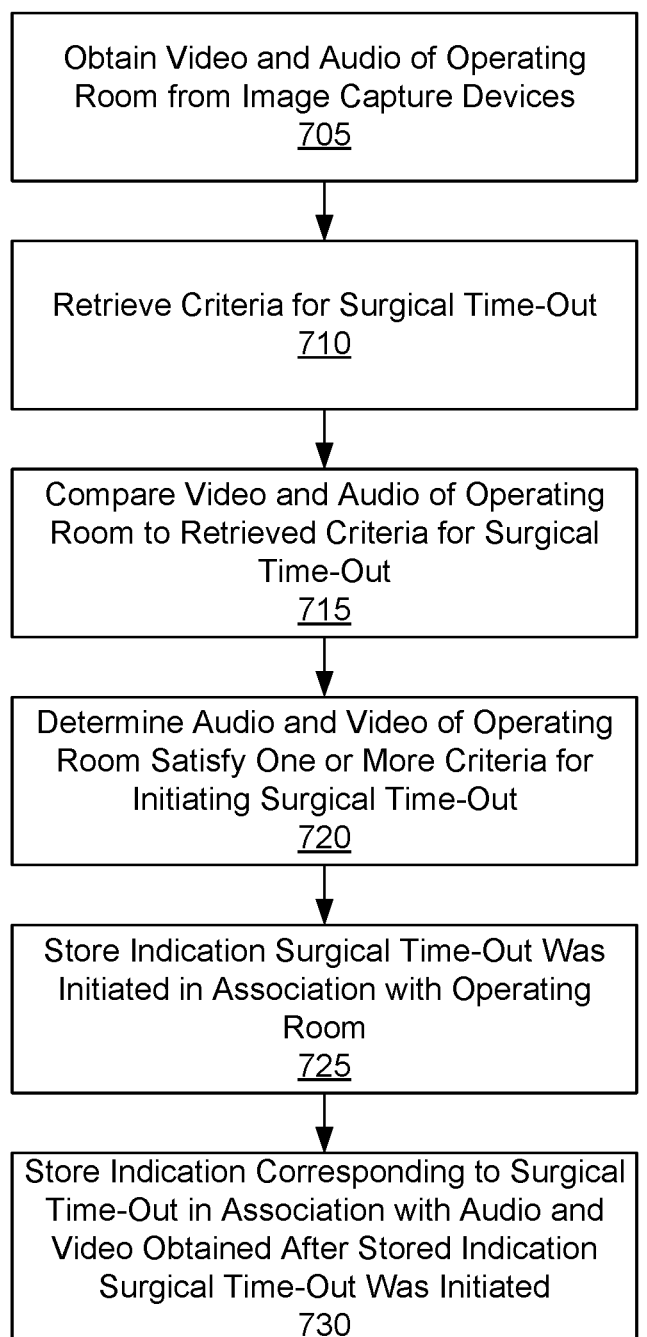

Obtain Video and Audio of Operating
Room from Image Capture Devices
705

Retrieve Criteria for Surgical Time-Out
710

Compare Video and Audio of Operating
Room to Retrieved Criteria for Surgical
Time-Out
715

Determine Audio and Video of Operating
Room Satisfy One or More Criteria for
Initiating Surgical Time-Out
720

Store Indication Surgical Time-Out Was
Initiated in Association with Operating
Room
725

Store Indication Corresponding to Surgical
Time-Out in Association with Audio and
Video Obtained After Stored Indication
Surgical Time-Out Was Initiated
730

FIG. 7

DETECTION AND EVALUATION OF A SURGICAL TIME-OUT CONFIRMING SURGICAL DETAILS FROM CAPTURED VIDEO OF AN OPERATING ROOM

BACKGROUND

This invention relates generally to monitoring an operating room, and more specifically to determining a phase of the operating room from captured video of the operating room.

When performing a surgical procedure in an operating room, personnel involved in the surgical procedure and in the operating room initially perform a "surgical time-out" before beginning the surgical procedure. During the surgical time-out, information about the surgical procedure and the personnel involved in the surgical procedure is audibly presented by personnel in the operating room. For example, the patient's identity is audibly confirmed, the surgical procedure being performed is audibly identified, a surgical site for the surgical procedure is audibly identified, and identities and roles of personnel involved in the surgical procedure are audibly identified. The initial surgical time-out reduces a likelihood of incorrect performance of the surgical procedure (e.g., performing the surgical procedure at an incorrect surgical site) and confirms appropriate equipment is available before the surgical procedure begins.

Conventionally, performance of a surgical time-out is manually indicated by one of the surgical personnel in the operating room to identify its completion, allowing a hospital or medical facility to maintain a record of performance of the surgical time-out. Such manual identification provides limited information about the completeness or accuracy of the surgical time-out, as surgical personnel may identify the surgical time-out as completed even if the surgical time-out was incompletely performed. Maintaining accurate information describing performance of a surgical time-out provides information for the surgical personnel or medical facility including the operating room for subsequent review of the surgical procedure for accuracy.

SUMMARY

Multiple image capture device are positioned at different locations within an operating room so the combination of image capture devices captures video of an entirety of the operating room or at least a portion of the operating room of interest. Additionally, different image capture devices may be positioned within the operating room to provide overlapping views of certain locations within the operating room. For example, a plurality of image capture devices capture video of a surgical table in the operating room, another plurality of image capture devices capture video of an instrument table in the operating room, while one or more image capture devices capture video of a door to enter or to exit the operating room. In some embodiments, each image capture device captures independent video of a portion of the operating room, while in other embodiments, video captured from a set of image capture devices is combined by the surgical tracking server to generate a three-dimensional reconstruction of the operating room, or of a portion of the operating room. Each image capture device captures both video and audio of the operating room in various embodiments. The image capture devices are configured to communicate the captured video to a surgical tracking server.

In some embodiments, various other sensors are included in the operating room other types of sensors are included in the operating room and are configured to communicate with the surgical tracking server. For example, one or more audio capture devices or microphones are positioned within the operating room to capture audio within the operating room. As another example, one or more lidar sensors are positioned at locations within the operating room to determine distances between the lidar sensors and objects within the operating room. In another example, one or more wireless transceivers (e.g., BLUETOOTH®) are positioned within the operating room and exchange data with client devices within the operating room. From signal strengths detected by different wireless transceivers when communicating with a client device, the surgical tracking server determines a location of the client device within the operating room through triangulation or through any other suitable method. As another example, one or more radio frequency identification (RFID) readers are included in the operating room to identify objects in the operating room coupled to, or including, RFID tags and to communicate information identifying the objects to the surgical tracking server. One or more temperature sensors determine a temperature or a humidity of the operating room and transmit the determined temperature or pressure to the surgical tracking server. However, in various embodiments, any type or combination of types of sensors are included in the operating room and configured to communicate with the surgical tracking server, providing various types of data describing conditions inside the operating room to the surgical tracking server.

The surgical tracking server obtains video of an operating room captured by the plurality of image capture devices positioned within the operating room. The image capture devices capture video and audio in various embodiments, and the surgical tracking server obtains the video and audio. In various embodiments, the surgical tracking server obtains an operating room identifier along with the video data, allowing the surgical tracking server identify an operating room for which the video data is obtained. In some embodiments, the surgical tracking server receives additional data describing the operating room from other sensors included in the operating room and communicating with the surgical tracking server. For example, the surgical tracking server obtains audio from one or more audio capture devices located within the operating room or obtains temperature or humidity data from one or more temperature sensors located in the operating room.

When performing a surgical procedure in an operating room, personnel involved in the surgical procedure and in the operating room initially perform a "surgical time-out" before beginning the surgical procedure. During the surgical time-out, information about the surgical procedure and the personnel involved in the surgical procedure is audibly presented by personnel in the operating room. In various embodiments, during the surgical time-out, the patient's identity is audibly confirmed, the surgical procedure being performed is audibly identified, a surgical site for the surgical procedure is audibly identified, and identities and roles of personnel involved in the surgical procedure are audibly identified. The surgical tracking server identifies performance of the surgical time out from video and audio obtained from image capture devices or other sensors within the operating room, allowing automatic identification of the surgical time-out.

To identify the surgical time-out, the surgical tracking server retrieves criteria for a surgical time-out. In various embodiments, the surgical tracking server stores the criteria for the surgical time-out, while in other embodiments, the surgical tracking server retrieves the criteria for the surgical time out from another source (e.g., a third party system external to the surgical tracking server, an analytics server, a remote storage device, etc.). In various embodiments, the criteria for the surgical time-out comprise a library of words or phrases corresponding to initiation of a surgical time-out. In other embodiments, the criteria for the surgical time-out includes poses or positions of people within the operating room corresponding to the surgical time-out, as well as words or phrases.

The surgical tracking server compares video and audio of the operating room to the one or more criteria for the surgical time-out. In response to the comparison determining audio or video satisfy one or more criteria for initiating the surgical time out, the surgical tracking server stores an indication that the surgical time-out was initiated in association with an identifier of the operating room and an identifier of the surgical procedure being performed in the operating room and stores an indication that video and audio obtained at and after a time when audio or video satisfying the one or more criteria for initiating the surgical time out corresponds to the surgical time-out in association with the obtained video and audio. This allows the surgical tracking server to identify portions of video or audio corresponding to the surgical time-out. In various embodiments, the surgical tracking server applies one or more speech to text models or natural language processing models to audio corresponding to video of the operating room from the one or more image capture devices or from one or more audio capture devices included in the operating room to determine whether the audio includes one or more of the stored words or phrases satisfying one or more criteria for initiating the surgical time-out. Additionally or alternatively, the surgical tracking server obtains one or more criteria specifying specific gestures corresponding to initiation of the surgical time-out and determines whether video from the image capture devices includes gestures matching one or more of the specific gestures corresponding to initiation of the surgical time-out. Hence, based on determining that obtained audio or video satisfies one or more criteria for initiating the surgical time-out, the surgical tracking server stores an indication that the surgical time-out has been initiated with an identifier of the operating room. In some embodiments, the surgical tracking server also stores an identifier of the surgical procedure being performed in the operating room in association with the indication that the surgical time-out has been initiated and the identifier of the operating room, maintaining a record of initiation of the surgical time-out for different surgical procedures. Additionally, the surgical tracking server stores an indication that video or audio received after a time when video or audio of the operating room was determined to satisfy one or more criteria corresponding to initiation of the surgical time-out corresponds to the surgical time-out.

The surgical tracking server also obtains one or more criteria corresponding to ending of the surgical time-out and compares audio and video of the operating room to the one or more criteria corresponding to ending of the surgical time-out. In response to determining audio or video of the operating room satisfies a threshold amount of the one or more criteria corresponding to ending of the surgical time-out, the surgical tracking server 120 stops storing the indication that captured video or audio corresponds to the surgical time-out. In some embodiments, the surgical tracking server stores an ending indicator in association with a time of the audio or video when the audio or video was determined to satisfy the threshold amount of the one or more criteria corresponding to ending of the surgical time out. This allows the surgical tracking server to identify portions of obtained audio or video of the operating room corresponding to a surgical time-out.

From obtained video and audio identified as corresponding to the surgical time-out, the surgical tracking server or an analytics server coupled to the surgical tracking server generates one or more quality metrics describing the surgical time-out by applying one or more trained models to audio and video identified as corresponding to the surgical time-out and to stored quality criteria for the surgical time-out. In various embodiments, the surgical tracking server or the analytics server maintains a set of quality criteria for a surgical time-out, with different quality criteria identifying different information expected to be provided during the surgical time-out. Example quality criteria include audible identification of each person in the operating room participating in the surgical procedure and their role in a surgical procedure, audible identification of a patient's identity, audible identification of the surgical procedure to be performed, audible identification of a surgical site on which the surgical procedure is to be performed, audible identification of patient-specific concerns for anesthesia, audible identification of sterility of instruments to be used in the surgical procedure, audible identification of one or more steps in the surgical procedure (or other information describing the surgical procedure), and any other suitable information describing the surgical procedure. In various embodiments, different quality criteria include different words or phrases corresponding to different information. The surgical tracking server or the analytics server applies one or more trained models to audio and video identified as corresponding to the surgical time-out to compare the portions of audio and video identified as corresponding to the surgical time-out to the stored set of quality criteria for the surgical time-out, and generates a completion metric indicating completion of the surgical time-out in response to content from the audio and video identified as corresponding to the surgical time-out satisfying at least a threshold amount of the stored set of quality criteria. In some embodiments, the completion metric is a binary value that indicates whether or not the audio and video corresponding to the surgical time out satisfied the threshold amount of the stored set of quality metrics, while in other embodiments the completion metric is a score based on an amount of the quality criteria satisfied by the audio and video corresponding to the surgical time out. To determine the completion metrics, in various embodiments the analytics server or the surgical tracking server applies one or more speech to text methods or natural language processing methods to audio and video identified as corresponding to the surgical time-out to extract content from the audio and video identified as corresponding to the surgical time-out for comparison to the set of criteria.

The surgical tracking server or the analytics server may determine the quality metrics in near real-time in various embodiments and determine one or more of the quality metrics when video and audio indicated as corresponding to the surgical time-out is received. This allows the surgical tracking server or the analytics server to provide notifications to people in the operating room based on the quality metrics describing performance of the surgical time-out. In some embodiments, the surgical tracking server or the analytics server transmits a notification to a display in the operating room, with the notification displaying a message, symbol, or other information in response to the surgical tracking server or the analytics server determining that each identified person has identified themselves and their role in the surgical procedure. In some embodiments, an alternative notification is transmitted to the display to indicate that one or more identified people have not identified themselves or their role in the surgical procedure.

In some embodiments, one or more quality metrics for the surgical time-out evaluates attentiveness of identified people in the video of the operating room during portions of video identified as corresponding to the surgical time-out. For example, the surgical tracking server or the analytics server determines an ambient noise level during the video and audio corresponding to the surgical time-out from the captured video and audio corresponding to the surgical time-out and generates a quality metric by comparing the determined ambient noise level to a threshold or by identifying a range of ambient noise levels including the determined ambient noise level. In another example, the surgical tracking server or the analytics server determines an amount of motion by identified people in the portion of the video data corresponding to the surgical time-out, and generates a value quantifying the amount of motion. Hence, the surgical tracking server or the analytics server may use an amount of motion by identified people in the operating room as a proxy for a level of attentiveness by the identified people in the operating room during the surgical timeout. As another example, a quality metric identifies a number of identified people moving in and out of a region of the operating room, such as a region within a threshold distance of a surgical table or the operating room, by tracking different identified people in the obtained video corresponding to the surgical time-out. In some embodiments, the surgical tracking server or the analytics server maintains one or more time-out quality models that generates an overall quality metric for a surgical time-out from a combination of the previously described metrics, as well as any other suitable metrics determined from audio or video corresponding to the surgical time-out.

BRIEF DESCRIPTION OF THE DRAWINGS

FIG. 5 is a flowchart of a method for determining a phase of an operating room from video captured of the operating room, in accordance with an embodiment.

FIG. 7 is a flowchart of a method for identifying a surgical time-out from captured video of an operating room, in accordance with an embodiment.

The figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

System Architecture

Figure 1:
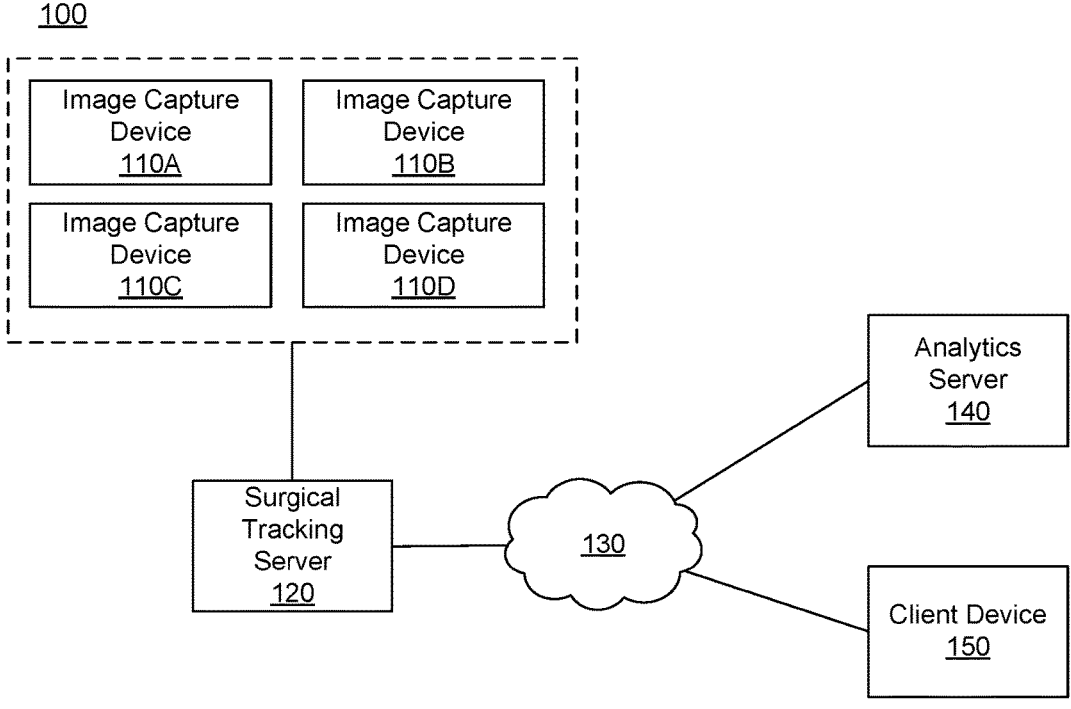
FIG. 1 is a block diagram of a system environment in which a surgical tracking server operates, in accordance with an embodiment.

FIG. 1 is a block diagram of one embodiment of a system environment 100 in which a surgical tracking server 120 operates, in accordance with an embodiment. The system environment 100 shown by FIG. 1 includes multiple image capture devices 110A, 110B, 110C, 110D (also referred to individually and collectively using reference number "110"), the surgical tracking server 120, a network 130, an analytics server 140, and a client device 150. In alternative configurations, different and/or additional components may be included in the system environment 100. Further, in some embodiments, functionality of certain components further described below may be combined into a single component.

Each image capture device 110 is configured to capture is configured to capture video (or images) of an area within a field of view of a corresponding image capture device 110. Multiple image capture device 110A, 110B, 110C, 110D are positioned at different locations within an operating room so the combination of image capture devices 110A, 110B, 110C, 110D captures video of an entirety of the operating room. Additionally, different image capture devices 110A, 110B, 110C, 110D may be positioned within the operating room to provide overlapping views of certain locations within the operating room, such as a surgical table in the operating room. In some embodiments, each image capture device 110 captures independent video of a portion of the operating room, while in other embodiments, video captured from a set of image capture devices 110 is combined by the surgical tracking server 120 to generate a three-dimensional reconstruction of the operating room, or of a portion of the operating room. Each image capture device 110 captures both video and audio of the operating room in various embodiments; for example, each image capture device 110 captures video and audio of the operating room using a real time streaming protocol (RTSP). Different image capture devices 110 may have fixed positions or may be configured to move within the operating room. Additionally, image capture devices 110 are capable of panning or zooming to alter video captured by the image capture devices 110.

Each image capture device 110 is configured to communicate with the surgical tracking server 120 to communicate video (and audio) captured by an image capture device 110 to the surgical tracking server 120. The image capture devices 110 are coupled to the surgical tracking server 120 through any suitable wireless or wired connection or combination of wireless or wired connections. In various embodiments, the surgical tracking server 120 is in a common physical location as the image capture devices 110. For example, the image capture devices 110 and the surgical tracking server 120 are in a common building or structure. In other examples, the surgical tracking server 120 is in a remote location from the image capture devices 110.

As further described below in conjunction with FIG. 3, the surgical tracking server 120 receives video from various image capture devices 110 and applies one or more computer vision methods to the video to identify regions of interest within the video, identify objects within the video, identify people or faces within the video. Additionally, from objects identified in the video and changes in positions of objects identified in the video, the surgical tracking server 120 determines a phase for the operating room. The phase for the operating room represents a state of objects within the operating room. For example, a phase indicates whether the operating room is in a pre-operative phase, an active surgical phase, a post-operative phase, a cleaning phase, or an available phase. Phases of the operating room and determination of a phase of the operating room from objects identified from the video is further described below in conjunction with FIG. 3. This allows the surgical tracking server 120 to leverage information from the captured video to determine a state of the operating room.

The network 130 may comprise any combination of local area and/or wide area networks, using both wired and/or wireless communication systems. In one embodiment, the network 130 uses standard communications technologies and/or protocols. For example, the network 130 includes communication links using technologies such as Ethernet, 802.11, worldwide interoperability for microwave access (WiMAX), 3G, 4G, code division multiple access (CDMA), digital subscriber line (DSL), etc. Examples of networking protocols used for communicating via the network 130 include multiprotocol label switching (MPLS), transmission control protocol/Internet protocol (TCP/IP), hypertext transport protocol (HTTP), simple mail transfer protocol (SMTP), and file transfer protocol (FTP). Data exchanged over the network 130 may be represented using any suitable format, such as hypertext markup language (HTML) or extensible markup language (XML). In some embodiments, all or some of the communication links of the network 130 may be encrypted using any suitable technique or techniques.

The analytics server 140 is coupled to the surgical tracking server 120 via the network 130 in various embodiments, while in other embodiments, the analytics server 140 is coupled to the surgical tracking server 120 through any suitable connection. In various embodiments, the analytics server 140 receives a phase of the operating room determined from the surgical tracking server 120. In some embodiments, the analytics server 120 also receives video captured by the image capture devices 110. From the phase of the operating room and information received from the surgical tracking server 120 in conjunction with the phase of the operating room, the analytics server 140 generates one or more analytics for the operating room. For example, the analytics server 140 receives a phase of the operating room and a timestamp indicating when the phase was determined from the surgical tracking server 120 and determines an amount of time the operating room has been determined to be in the phase. In various embodiments, the analytics server 140 also generates one or more metrics for the operating room based on the amount of time the operating room has been determined to be in the phase. In various embodiments, the analytics server 140 receives a phase determined for an operating room, an identifier of the operating room, and a time when the phase was determined from the surgical tracking server 120, allowing the analytics server 140 to generate and to maintain phases for multiple operating rooms. Generation of analytics for the operating room is further described below in conjunction with FIG. 4.

Additionally, the analytics server 140 generates notifications for transmission to client devices 150 via the network 130 and instructions for a client device 150 to generate an interface describing metrics or other analytic information generated by the analytics server 140. For example, the analytics server 140 transmits a notification to client devices 150 corresponding to one or more specific users when an operating room has a specific phase or has been in a specific phase for at least a threshold amount of time. This allows the analytics server 140 to push a notification to specific users to provide the specific users with information about an operating room. Similarly, instructions generated by the analytics server 140 and transmitted to a client device 150 cause the client device 150 to generate an interface describing metrics or analytic information generated by the analytics server 140 for one or more operating rooms. A user of the client device 150 may select one or more interfaces from the analytics server 140 to receive instructions for generating a specific interface displaying one or more metrics or other analytic information for one or more operating rooms generated by the analytics server 140. Interfaces or notifications generated by the analytics server 140 are further described below in conjunction with FIG. 4.

A client device 150 is one or more computing devices capable of receiving user input as well as transmitting and/or receiving data via the network 130. In one embodiment, the client device 150 is a conventional computer system, such as a desktop computer or a laptop computer. Alternatively, the client device 150 may be a device having computer functionality, such as a personal digital assistant (PDA), a mobile telephone, a smartphone or another suitable device. A client device 150 is configured to communicate with other devices via the network 130. In one embodiment, the client device 150 executes an application allowing a user of the client device 150 to interact with the analytics server 140 or with the surgical tracking server 120. For example, the client device 150 executes a browser application to enable interaction with the analytics server 140 or with the surgical tracking server 120 via the network 130. In another embodiment, a client device 150 interacts with the analytics server 140 or with the surgical tracking server 120 through an application programming interface (API) running on a native operating system of the client device 150, such as IOS® or ANDROID™.

Figure 2:
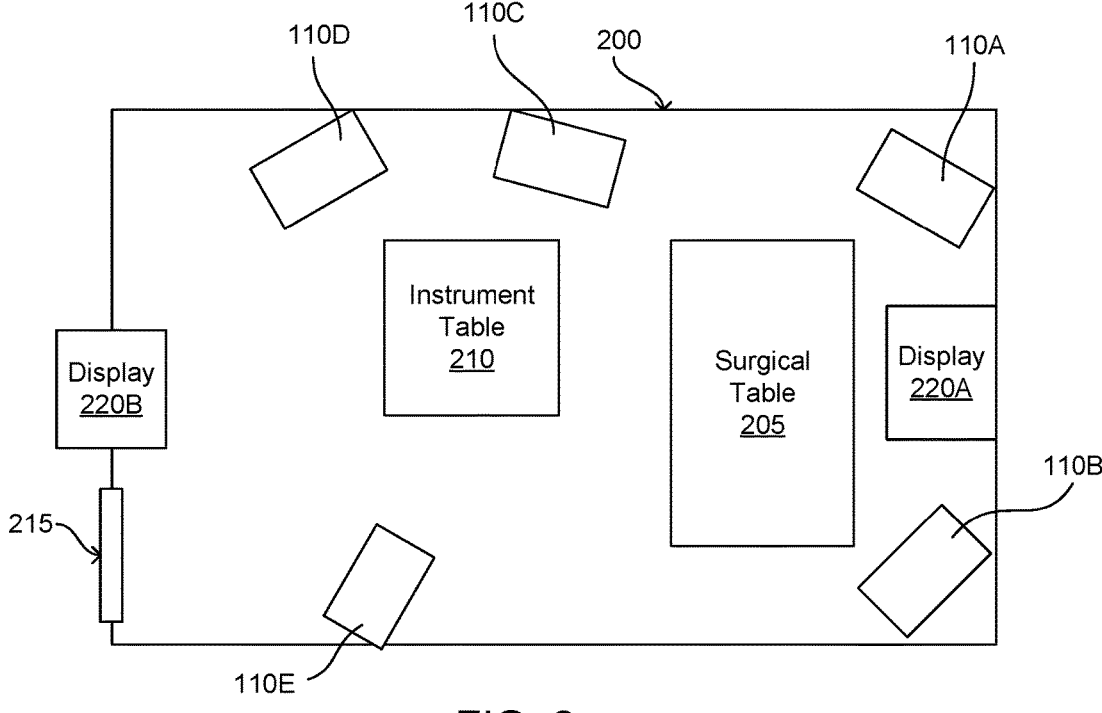
FIG. 2 is an example configuration of image capture devices in an operating room for capturing video transmitted to a surgical tracking server, in accordance with an embodiment.

FIG. 2 is an example configuration of image capture devices 110 in an operating room 200 for capturing video transmitted to a surgical tracking server 120. In the example of FIG. 2, the operating room 200 includes a surgical table 205, an instrument table 210, and a door 215, although additional equipment is included in the operating room 200 in different configurations or implementations. Further, while the example shown in FIG. 2 shows five image capture devices 110A, 110B, 100C, 110D, 110E (also referred to individually and collectively using reference number 110), in other embodiments any suitable number of image capture devices 110 are included in the operating room 200.

The image capture devices 110A, 110B, 110C, 110D, 110E are placed at different locations within the operating room 200 so a combination of video captured by image capture devices 110A, 110B, 110C, 110D, 110E includes an entire area within the operating room 200. Additionally, different image capture devices 110A, 110B, 110C, 110D, 110E are positioned so specific objects within the operating room 200 are within a field of view of particular image capture devices 110A, 110B, 110C, 110D, 110E. In the example of FIG. 2, image capture devices 110A and 110B are positioned so the surgical table 205 is within a field of view of both image capture device 110A and image capture device 110B. At least a portion of a field of view of image capture device 110A overlaps with at least a portion of a field of view of image capture device 110B in some embodiments, providing overlapping fields of view of the surgical table 205 from different image capture devices 110A, 110B. In some embodiments, image capture device 110A, image capture device 110B, or an additional image capture device 110 is located in or coupled to a surgical light proximate to the surgical table 205 and configured to illuminate a portion of a surgical area on the surgical table 205, allowing an image capture device 110 to capture video of the surgical area. Similarly, image capture devices 110C, 110D are positioned so fields of view of both image capture device 110C and image capture device 110D include the instrument table 210. In some embodiments, at least a portion of a field of view of image capture device 110C overlaps with at least a portion of a field of view of image capture device 110D, providing overlapping fields of view of the instrument table 210. Further, one or more image capture devices 110 may be coupled to or included in one or more surgical instruments, such as a laparoscope, and configured to communicate video to the surgical tracking server 120. In various embodiments, the image capture devices 110 are positioned below a level of light fixtures in the operating room 200 to improve illumination of video captured by the image capture devices 110.

Additionally, in the example shown by FIG. 2, image capture device 110E is positioned within the operating room 200 so a field of view of image capture device 110E includes a door 215 providing ingress and egress to the operating room 200. Image capture device 110E has a field of view capable of capturing people entering and exiting the operating room 200 through the door 215 and capturing opening and closing of the door 215. While FIG. 2 shows an example with a single image capture device 110E capturing video of the door 215, in other embodiments, multiple image capture devices 110 are positioned to have fields of view including the door 215. Additionally, in environments where the operating room 200 includes multiple points of entry or exit, image capture devices 110 are positioned so various image capture devices 110 include fields of view including the multiple points of entry or exit. For example, each point of entry or exit is within a field of view of at least one image capture device 110 in various embodiments.

In the example shown by FIG. 2, the operating room 200 also includes displays 220A, 220B. Each display 220A, 220B is communicatively coupled to the surgical tracking server 120 or to the analytics server 140. A display 220A, 220B receives a notification or instructions from the surgical tracking server 120 or the analytics server 140 and displays information based on the received notification or instructions. For example, display 220B is positioned proximate to the door 215 and is visible from outside of the operating room 200, in response to receiving a specific instruction from the surgical tracking server 120 or the analytics server 140, display 220B displays a message not to open the door 215 to prevent people outside of the operating room 200 from opening the door. As another example, display 220A is visible from the surgical table and displays a timer in response to information from the surgical tracking server 120 or the analytics server 140, with the timer indicating an amount of time that the operating room 200 has been in a phase determined by the surgical tracking server. Other information, such as messages to people inside the operating room 200, instructions for operating equipment in the operating room 200, or any other suitable information may be displayed by display 220A, 220B based on instructions or notifications received from the surgical tracking server 120 or the analytics server 140.

While FIG. 2 shows an example where the operating room 200 includes multiple image capture devices 110, in various embodiments, other types of sensors are included in the operating room 200 and configured to communicate with the surgical tracking server 120. For example, one or more audio capture devices or microphones are positioned within the operating room 200 to capture audio within the operating room 200. As another example, one or more lidar sensors are positioned at locations within the operating room to determine distances between the lidar sensors and objects within the operating room. In another example, one or more wireless transceivers (e.g., BLUETOOTH®) are positioned within the operating room 200 and exchange data with client devices 150 within the operating room 200; from signal strengths detected by different wireless transceivers when communicating with a client device 150, the surgical tracking server 120 determines a location of the client device 150 within the operating room 200 through triangulation or through any other suitable method. As another example, one or more radio frequency identification (RFID) readers are included in the operating room 200 to identify objects in the operating room coupled to, or including, RFID tags and to communicate information identifying the objects to the surgical tracking server 120. One or more temperature sensors determine a temperature or a humidity of the operating room 200 and transmit the determined temperature or pressure to the surgical tracking server 120. However, in various embodiments, any type or combination of types of sensors are included in the operating room 200 and configured to communicate with the surgical tracking server 120, providing various types of data describing conditions inside the operating room 200 to the surgical tracking server 120.

Figure 3:
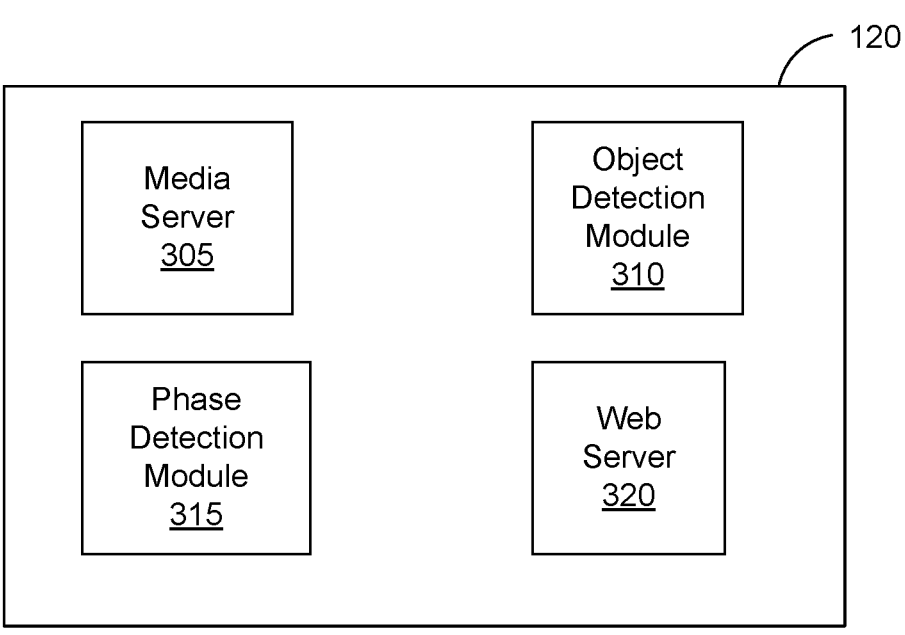
FIG. 3 is a block diagram of a surgical tracking server, in accordance with an embodiment.

FIG. 3 is a block diagram of a surgical tracking server 120, in accordance with an embodiment. The surgical tracking server 120 shown in FIG. 3 includes a media server 305, an object detection module 310, a phase detection module 310, and a web server 320. In other embodiments, the surgical tracking server 120 may include additional, fewer, or different components for various applications. Conventional components such as network interfaces, security functions, load balancers, failover servers, management and network operations consoles, and the like are not shown so as to not obscure the details of the system architecture.

The media server 305 receives video captured by the one or more video capture devices 110. When an operating room includes additional types of sensors, the media server 305 also receives data from other sensors included in the operating room. In various embodiments, the media server 305 establishes a connection to one or more video capture devices 110 using real time streaming protocol (RTSP). The media server 305 also transmits instructions to the one or more video capture devices 110 in some embodiments, such as instructions to reposition a field of view of an image capture device 110 or instructions to change a magnification level of an image capture device. Additionally, the media server 205 may transmit instructions to other sensors in an operating room that are coupled to the surgical tracking server 120, allowing the media server to adjust operation of various sensors in the operating room through any suitable protocols or formats.

The object detection module 310 applies one or more models to the captured video data to identify one or more regions within frames of video from the one or more image capture devices 110 that include objects, including people, instruments, equipment, or other objects. For example, the one or more models perform two- or three-dimensional pose tracking, allowing the object detection module 310 to identify regions of video data including an object based on the pose tracking. In various embodiments, the object detection module 310 performs facial tracking (in two-dimensions or in three-dimensions), two-dimensional pose tracking, three-dimensional pose tracking, or any other suitable method to identify portions of a person's face or portions of the person's body within video from one or more image capture devices 110. The object detection module 310 identifies regions of video including objects and stores metadata in association with the video data specifying locations within the video of the identified regions. For example, the object detection module 310 stores coordinates of frames of the video specifying a bounding box identified as including an object, so the bounding box specifies the region of the video including the object.

Additionally, the object detection module 310 applies one or more object detection methods to video data from one or more image capture devices 310 to identify objects in frame of the video. The object detection module 310 also identifies locations of identified objects in frames of video in various embodiments. For example, the object detection module 310 generates a bounding box surrounding each object identified in a frame. In various embodiments, the object detection module 310 uses one or more object detection methods to identify objects within frames of video data and to generate bounding boxes corresponding to each of the identified objects. When identifying objects, the object detection module 310 may also identify a category or a type for each identified object. For example, an object detection method applied by the object detection module 310 associates different categories with objects based on characteristics of the objects and associates a type or a category from the object detection method with an identified object.

In some embodiments, the object detection module 310 compares each object identified with frames of video to stored images of equipment or items included in an operating room. The object detection module 310 maintains a library of images corresponding to different equipment or items provided by one or more users or obtained from any suitable source. When comparing an object identified within previously obtained images of items or equipment, the object detection module 310 determines confidences of the identified object matching different items or equipment by applying a classification model to the identified object and to the images of equipment or items. The object detection module 310 may train the classification model to determine a likelihood of an object identified from a frame of video matching an item or equipment based on prior matching of objects in video to different items or equipment. For example, the object detection module 310 applies a label indicating an item or equipment matching an object identified from video to characteristics of the object identified from the video. From the labeled characteristics of objects extracted from video the object detection module 310 trains the classification model using any suitable training method or combination of training methods (e.g., back propagation to train the classification model if it is a neural network, curve fitting techniques if the classification model is a linear regression). After training, the object detection module 310 applies the trained classification model to characteristics of objects identified within video, and the classification model outputs confidences of the object matching different items or equipment. Based on the confidences output by the classification model, the object detection module 310 determines an item or equipment corresponding to an identified object. For example, the object detection module 310 determines an identified object is an item or equipment for which the classification model output a maximum confidence.

From objects detected by the object detection module 310 within video of the operating room from the image capture devices 110, the phase detection module 315 determines a phase of the operating room. The phase for the operating room represents a state of objects within the operating room. For example, a phase indicates whether the operating room is in a pre-operative phase, an active surgical phase, a post-operative phase, a cleaning phase, or an available phase. Different phases of the operating room may include one or more sub-phases identified by the phase detection module 315 to more particularly identify a status of objects within the operating room from captured video of the operating room, as well as data from one or more other types of sensors included in the operating room.

In some embodiments, the phase detection module 315 receives video and an identifier of objects included in the video data from the object detection module 310. The phase detection module 315 determines a state of one or more of the identified objects within the video by applying one or more trained models to the video and the identified objects. Example objects for which the phase detection module 315 determines a state include: people in the operating room, tables in the operating room, surfaces in the operating room on which instruments are placed, cleaning equipment in the operating room, diagnostic equipment in the operating room, and any other suitable object included in the operating room. An example state of a person in the operating room indicates whether the person is scrubbed or unscrubbed; in another example, a state of a patient in the operating room indicates whether or not the patient is draped for surgery. An example state of a table in the operating room indicates whether the table is bare, is ready to be occupied by a patient, is occupied by a patient, or is unoccupied. An example state of an instrument surface indicates whether the instrument surface is prepared or is unprepared, while another example state of an instrument surface indicates whether the instrument surface is sterilized or is not sterilized. In various embodiments, the phase detection module 315 trains models to determine states of various objects identified in video by the object detection module 310 based on states previously determined for an object or for a person from video, allowing the model to determine a state of an object or a person based on characteristics of video including the object or the person. For example, the object detection module 310 applies a label indicating a state of an object or a person to characteristics of video (or other data from sensors) including the object or the person. From the labeled characteristics, the phase detection module 315 trains a model using any suitable training method or combination of training methods (e.g., back propagation to train the classification model if it is a neural network, curve fitting techniques if the classification model is a linear regression). After training, the phase detection module 315 applies the trained model to characteristics of video (or to other sensor data) including an identified object to output a state of the identified object.

From the states determined for various identified objects, the phase detection module 315 determines a phase for the operating room. In some embodiments, the phase detection module 315 maintains a set of rules associating different phases for the operating room with different combinations of states determined for objects in the operating room. Alternatively, the phase detection module 315 includes a trained phase classification model that receives as inputs states determined for various identified objects and outputs a phase for the operating room from the determined states. The phase detection module 315 may train the phase classification model to determine a likelihood of a combination of states of objects matching a phase based on prior matching of combinations of states to phases. For example, the phase detection module 315 applies a label indicating a combination of states of objects matching a phase. From the labeled combinations of states of objects, phase detection module 315 trains the phase classification model using any suitable training method or combination of training methods (e.g., back propagation to train the classification model if it is a neural network, curve fitting techniques if the classification model is a linear regression).

In various embodiments, the phase detection module 315 also includes stored criteria for a surgical time-out and compares a portion of the video obtained from the image capture device 110 to the stored criteria to determine whether the surgical time-out was performed. During the surgical time-out, information about a surgical procedure being performed in the operating room and the personnel involved in the surgical procedure is audibly presented by personnel in the operating room. For example, during the surgical time-out, the patient's identity is audibly confirmed, the surgical procedure being performed is audibly identified, a surgical site for the surgical procedure is audibly identified, and identities and roles of personnel involved in the surgical procedure are audibly identified. In various embodiments, the phase detection module 315 stores a library of words or phrases corresponding to initiation of a surgical time-out. Through one or more speech to text models or natural language processing of audio corresponding to video of the operating room from the one or more image capture devices 110 or from one or more audio capture devices included in the operating room, the phase detection model 315 determines whether the audio includes one or more of the stored words or phrases corresponding to initiation of the surgical time-out. Additionally or alternatively, the phase detection module 315 stores a set of specific gestures corresponding to initiation of the surgical time-out and determines whether video from the image capture devices 110 includes one or more of the specific gestures corresponding to initiation of the surgical time-out. Hence, based on determining that captured audio or video including an indication that the surgical time-out has been initiated, the phase detection model 315 stores an indication that video or audio received after detection of the indication that the surgical time-out has been initiated is a surgical time-out. The phase detection module 315 similarly includes one or more conditions that, when satisfied, indicate the surgical time-out has ended. In response to determining audio or video of the operating room satisfies one or more of the conditions, the phase detection module 315 stops storing the indication that captured video or audio corresponds to the surgical time-out. This allows the phase detection module 315 to identify portions of captured audio or video of the operating room corresponding to a surgical time-out. In some embodiments, a portion of video or audio data corresponding to the surgical time out is transmitted to the analytics server 140, which generates one or more metrics describing the surgical time-out, as further described below in conjunction with FIG. 4; however, in other embodiments, the phase detection module 315 generates the one or more metrics describing the surgical time-out.

As further described below in conjunction with FIG. 4, the phase of the operating room determined by the phase detection module 315 is transmitted to the analytics server 140, which determines additional information describing the operating room from the determined phase. For example, the phase detection module 315 communicates an identifier of an operating room, a phase determined for the operating room, and a time when phase was determined for the operating room to the web server 320 for transmission to the analytics server 140. In other embodiments, the phase detection module 315 communicates any suitable information to the analytics server 140.

The web server 320 links the surgical tracking server 120 via the network 130 to the analytics server 140 or to one or more client devices 150. Additionally, the web server 320 may exchange information between the surgical tracking server 120 and the analytics server 140. The web server 320 serves web pages, as well as other content, such as JAVA®, FLASH®, XML, and so forth. The web server 320 may receive and route messages between the analytics server 140 or one or more client devices 150 and or to the surgical tracking server 120. A user may send a request to the web server 320 from a client device 150 for specific information maintained by the surgical tracking server 120. Additionally, the web server 320 may provide application programming interface (API) functionality to send data directly to native client device operating systems, such as IOS®, ANDROID™, WEBOS® or BlackberryOS.

Figure 4:
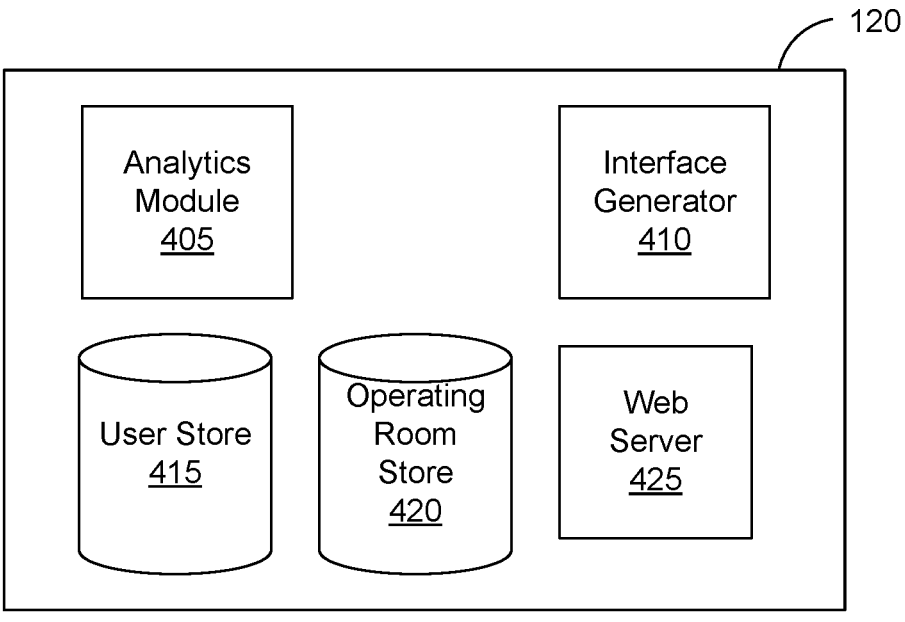
FIG. 4 is a block diagram of an analytics server, in accordance with an embodiment.

FIG. 4 is a block diagram of an analytics server 140, in accordance with an embodiment. The analytics server 140 shown in FIG. 4 includes an analytics module 405, an interface generator 410, a user store 415, an operating room store 420, and a web server 425. In other embodiments, the analytics server 140 may include additional, fewer, or different components for various applications. Conventional components such as network interfaces, security functions, load balancers, failover servers, management and network operations consoles, and the like are not shown so as to not obscure the details of the system architecture. In some embodiments, the functionality described in conjunction with the analytics server 140 is also provided by the surgical tracking server 120, allowing a single device to provide the functionality of the analytics server 140 and the surgical tracking server 120.

The analytics module 405 receives information describing an operating room, including a phase of the operating room, from the surgical tracking server 120 and generates one or more metrics describing the operating room. For example, the analytics module 405 receives an identifier of an operating room, a phase determined for the operating room, and a time when the phase was determined for the operating room from the surgical tracking server 120. From the received information, the analytics module 405 determines a duration that the operating room has been in a particular phase. Similarly, the analytics module 405 identifies a time when the operating room changes from a phase to a different phase. In some embodiments, the analytics module 405 compares a determined duration that the operating room has been in a particular phase to a desired duration and generates a metrics based on the comparison. The metric indicates whether the operating room has been in the particular phase longer than the desired duration in some embodiments. The analytics module 405 maintains different desired durations for different phases in various embodiments and may maintain desired durations for different combinations of phases and operating room, allowing a generated metric to reflect characteristics of a particular operating room.

In various embodiments, the analytics module 405 generates one or more quality metrics for video or audio data from the surgical tracking server 120 having an indication that the video or audio corresponds to a surgical time-out. The analytics module 405 maintains a set of criteria for a surgical time-out, with different criteria identifying different information expected to be provided during the surgical time-out. Example criteria include audible identification of each person in the operating room participating in the surgical procedure and their role in a surgical procedure, audible identification of a patient's identity, audible identification of the surgical procedure to be performed, audible identification of a surgical site on which the surgical procedure is to be performed, audible identification of patient-specific concerns for anesthesia, audible identification of sterility of instruments to be used in the surgical procedure, audible identification of one or more steps in the surgical procedure (or other information describing the surgical procedure), and any other suitable information describing the surgical procedure. In various embodiments, different criteria include different words or phrases corresponding to different information. For example, various criteria include names or descriptions of surgical procedures and names or descriptions of instruments. The analytics module 405 compares audio and video identified as corresponding to the surgical time-out to the stored set of criteria for the surgical time-out, and generates a quality metric indicating completion of the surgical time-out in response to content from the audio and video identified as corresponding to the surgical time-out satisfying at least a threshold amount of the stored set of criteria. The analytics module 405 applies one or more speech to text methods or natural language processing methods to audio and video identified as corresponding to the surgical time-out to extract content from the audio and video identified as corresponding to the surgical time-out for comparison to the set of criteria.

In some embodiments, to determine whether each person in the operating room participating in the surgical procedure identifies themselves and their roles in the surgical procedure, the analytics module 405 receives identification of regions of video of the operating room corresponding to each person participating in the surgical procedure. The analytics module 405 determines a region of the video corresponding to a person speaking for different audio during the audio and video identified as corresponding to the surgical time-out by application of one or more trained classification models to the video data. For each person identified as speaking, the analytics module 405 determines whether portions of audio from an identified person matches stored information identifying names and matching roles in a surgical procedure. The analytics module 405 stores a flag in association with each identified person that indicates whether portions of audio from the identified person matches stored information identifying names and matching roles in a surgical procedure. In response to the flag stored in association with each identified person indicating portions of audio from portions of audio from an identified person matches stored information identifying names and matching roles in a surgical procedure, the analytics module 405 determines that each identified person has identified themselves and their role in the surgical procedure. In some embodiments, the analytics module 405 transmits a notification to a display in the operating room, with the notification displaying a message, symbol, or other information in response to the analytics module 405 determining that each identified person has identified themselves and their role in the surgical procedure; in some embodiments, an alternative notification is transmitted to the display to indicate that one or more identified people have not identified themselves or their role in the surgical procedure.

In some embodiments, one or more quality metrics for the surgical time-out evaluates attentiveness of identified people in the video of the operating room during portions of video identified as corresponding to the surgical time-out. For example, the analytics module 405 determines an ambient noise level during the video and audio corresponding to the surgical time-out from the captured video and audio corresponding to the surgical time-out; a quality metric generated by the analytics module 405 indicates whether the determined ambient noise level exceeds a threshold or identifies a range of ambient noise levels including the determined ambient noise level. Based on comparison of the determined ambient noise level to the threshold or to a range, the analytics module 405 generates a quality metric identifying whether the determined ambient noise exceeded a threshold indicating an ambient noise level over which audio comprising the surgical time-out is likely to have been audible to the people in the operating room. In another example, the analytics module 405 determines an amount of motion by identified people in the portion of the video data corresponding to the surgical time-out, and generates a value quantifying the amount of motion. By comparing the value quantifying the amount of motion by identified people in the operating room, the analytics module 405 generates a quality metric representing a level of attentiveness of identified people in the operating room during the surgical time-out, with a lower value of the quality metric corresponding to greater amounts of motion and a higher value of the quality metric corresponding to lower amounts of motion. In some embodiments, the analytics module 405 generates an indication whether the quality metric representing a level of attentiveness equals or exceeds a threshold value. Hence, the analytics module 405 may use an amount of motion by identified people in the operating room as a proxy for a level of attentiveness by the identified people in the operating room during the surgical timeout. As another example, a quality metric identifies a number of identified people moving in and out of a region of the operating room, such as a region within a threshold distance of a surgical table or the operating room, by tracking different identified people in the obtained video corresponding to the surgical time-out. In some embodiments, the analytics module 405 maintains time-out quality model that generates an overall quality metric for a surgical time-out from a combination of the previously described metrics, as well as any other suitable metrics determined from audio or video corresponding to the surgical time-out.

Additionally, the analytics module 405 initiates generation of one or more notifications by the interface generator 410 based on a determined phase of the operating room. For example, the analytics module 405 stores a specific phase or sub-phase of the operating room during which the surgical time-out is performed. In response to receiving a phase, or sub-phase, of the operating room from the surgical tracking server 120 that is after the specific phase or the specific sub-phase without receiving video or audio data from the surgical tracking server 120 having an indication that the video or audio corresponds to a surgical time-out, the analytics module 405 provides instructions to the interface generator 410 to transmit a notification to one or more displays in the operating room displaying a prompt or a message to perform the surgical time-out. In other embodiments, the analytics server 405 maintains a predicted duration of a sub-phase or a phase in which the surgical time-out is performed based on durations of the sub-phase or phase from prior surgeries. In response to determining an operating room has been in the sub-phase or phase in which the surgical time-out is performed for a length of time that is within a threshold amount of time from the predicted duration of the sub-phase or phase and not receiving video or audio data from the surgical tracking server 120 having an indication that the video or audio corresponds to a surgical time-out, the analytics module 405 provides instructions to the interface generator 410 to transmit a notification to one or more displays in the operating room displaying a prompt or a message to perform the surgical time-out.

From analytical information or metrics determined by the analytics module 405, the interface generator 410 generates one or more notifications or instructions for a client device 150 to render an interface. In various embodiments, the interface generator 410 includes one or more criteria and generates a notification for transmission to a client device 150 of a user when metrics or analytical information generated by the analytics module 405 satisfy at least a threshold amount of criteria. Different criteria may be maintained for different operating rooms in various embodiments. For example, the interface generator 410 retrieves criteria from the operating room store 420 from an operating room identifier and compares metrics from the analytics module 405 to the retrieved criteria for the operating room. The criteria for an operating room include information identifying a user to whom a notification is transmitted in various embodiments. In some embodiments, the surgical tracking server 120 or the analytics server 140 transmits a notification to a specific user in response to an amount of time the operating room has been in a determined phase equals or exceeds a threshold duration. In some embodiments, the threshold duration is based on a type of surgery determined for the operating room. As another example, the interface generator 410 includes instructions for rendering an interface displaying one or more metrics for an operating room. For example, an interface includes identifiers of different phases and displays a duration that an operating room has been determined to be in each of the different phases; the interface displays an indication whether the operating room has been in a determined phase for greater than a desired duration in some embodiments. However, the interface generator 410 includes instructions for generating any suitable interface to present metrics or other analytical data from the analytics module 405 to users or for transmitting notifications to client devices 150 of users when metrics or other analytical information from the analytics module satisfy one or more criteria.

The user store 415 includes a user profile for each user of the analytics server 140 or of the surgical tracking server 120. A user profile includes a user identifier uniquely identifying the user and may include any other information describing the user (e.g., a username, descriptive information of the user, etc.). Additionally, a user profile for a user identifies which operating rooms about which the user is authorized to obtain data from the surgical tracking server 120 or from the analytics server 140. In some embodiments, a user profile identifies a type of a user. Different types of users receive different information from the analytics server 140 or from the surgical tracking server 120. For example, a user having a type identified as a nurse receives notifications from the analytics server 140 when an operating room is in one or more particular phases. As another example, a user having a type identified as an administrator is authorized to retrieve interfaces displaying durations that various operating rooms have been in one or more phases. Hence, users having different types may be authorized to access different data from the analytics server 140 or from the surgical tracking server 120, allowing the analytics server 140 or the surgical tracking server 120 to provide different users with access to different information.

Additionally, a user profile for a user may include one or more images identifying the user. In some embodiments, the surgical tracking server 120 retrieves images of users from user profiles and compares facial data or other user data from captured video to identify one or more users in the video. Other identifying information may be stored in a user profile for a user, allowing the surgical tracking server 120, or the analytics server 140, to identify users included in video data or other data captured by sensors included in the operating room. Users having a certain type, such as a type indicating a user is a surgeon, may store preference information in a corresponding user profile, with the preference information specifying one or more configurations in the operating room. For example, preference information for a surgeon identifies instruments to include on an instrument table for the surgeon and may specify a placement of instruments on the instrument table relative to each other. Identifying a particular user who is a surgeon from captured video or other data allows the surgical tracking server 120 to retrieve the preference information of the surgeon for use in preparing the operating room for the surgeon. Multiple sets of preference information may be maintained for a user, with different preference information corresponding to different types of surgeries, allowing a user to specify preferred instruments and instrument placement for a variety of surgeries.

The operating room store 420 includes an operating room profile for each operating room for which the surgical tracking server 120 obtains video (or other data). A profile for an operating room includes an operating room identifier that uniquely identifies the operating room. In association with an operating room identifier, the operating room profile includes metrics or other analytical data generated by the analytics module 405. In some embodiments, the operating room profile includes metrics or other analytical data generated within a threshold time interval of a current time. Additionally, the operating room profile for an operating room includes a schedule for the operating room that indicates dates and times when surgeries using the operating room are scheduled or when the operating room is otherwise in use. The schedule for an operating room is obtained from one or more users authorized to provide scheduling information for the operating room, such as users having one or more specific types. The schedule for an operating room identifies users or patients scheduled to be in the operating room during a time interval, as well as a description of a procedure or surgery to be performed during the time interval. This allows the operating room profile to provide information describing planned use of an operating room corresponding to the operating room profile. In other embodiments, additional information may be included in an operating room profile.

The web server 425 links the analytics server 140 via the network 130 to the surgical tracking server 120 or to one or more client devices 150. Additionally, the web server 425 may exchange information between the surgical tracking server 120 and one or more client devices 150. The web server 425 serves web pages, as well as other content, such as JAVA®, FLASH®, XML and so forth. The web server 425 may receive and route messages between the analytics server 140 or one or more client devices 150 or to the surgical tracking server 120. A user may send a request to the web server 425 from a client device 150 for specific information maintained by the analytics server 140. Similarly, the web server 425 may transmit a notification or instructions for generating an interface to a client device 150 to display or to otherwise present content from the analytics server 140 to a user via the client device 150. Additionally, the web server 425 may provide application programming interface (API) functionality to send data directly to native client device operating systems, such as IOS®, ANDROID™, WEBOS® or BlackberryOS.

Determining Operating Room Phase

FIG. 5 is a flowchart of one embodiment of a method for determining a phase of an operating room from video captured of the operating room. In other embodiments, the method includes different or additional steps than those described in conjunction with FIG. 5. Further, in some embodiments, steps of the method are performed in different orders than the order described in conjunction with FIG. 5.

A surgical tracking server 120, further described above in conjunction with FIGS. 1 and 3, obtains 505 video of an operating room captured by a plurality of image capture devices 110 positioned within the operating room. As further described above in conjunction with FIGS. 1 and 2, different image capture devices 110 have different positions within an operating room and are positioned to capture video of different locations within the operating room. Each image capture device 110 is configured to communicate with the surgical tracking server 120, which receives video of the operating room captured by each image captured device 110 positioned within the operating room. In various embodiments, the surgical tracking server 120 obtains an operating room identifier along with the video data, allowing the surgical tracking server 120 identify an operating room for which the video data is obtained 505. In some embodiments, the surgical tracking server 120 receives additional data describing the operating room from other sensors included in the operating room and communicating with the surgical tracking server 120. Examples of additional sensors included in the operating room from which the surgical tracking server 120 obtains 505 data include: audio capture devices, lidar sensors, wireless transceivers, example, radio frequency identification (RFID), temperature sensors, or any other suitable type of sensor.

The surgical tracking server 120 identifies 510 regions within frames of video from one or more image capture devices 110 including people or including other objects. In various embodiments, the surgical tracking server 120 applies one or more computer vision methods or models to the captured video data to identify the one or more regions within frames of video including objects. As used herein, "objects" includes people, equipment, instruments, or other items. For example, the one or more models perform two- or three-dimensional pose tracking, allowing the identification of regions of video data including a person or other object based on the pose tracking. In various embodiments, surgical tracking server 120 performs facial tracking (in two-dimensions or in three-dimensions), two-dimensional pose tracking, three-dimensional pose tracking, or any other suitable method to identify portions of a person's face or portions of the person's body within video from one or more image capture devices 110. One or more object detection methods may be applied by the surgical tracking server 120 to identify 510 objects in frame of the video, as further described above in conjunction with FIG. 3. To subsequently identify regions within a frame of video including an object or a person, the surgical tracking server 120 stores metadata in association with the video data identifying a frame including an identified object and coordinates within the frame specifying a bounding box identified as including a person or another object, so the bounding box specifies the region of the video including the person or the other object.

The surgical tracking server 120 determines 515 a state of one or more of the identified objects within the video by applying one or more trained models to the video and the identified objects. Example objects for which the surgical tracking server 120 determines 515 a state include: people in the operating room, tables in the operating room, surfaces in the operating room on which instruments are placed, cleaning equipment in the operating room, diagnostic equipment in the operating room, and any other suitable object included in the operating room. An example state of a person in the operating room indicates whether the person is scrubbed or unscrubbed. In another example, a state of a patient in the operating room indicates whether or not the patient is draped for surgery. An example state of a table in the operating room indicates whether the table is bare, is ready to be occupied by a patient, is occupied by a patient, or is unoccupied. An example state of an instrument surface indicates whether the instrument surface is prepared or is unprepared, while another example state of an instrument surface indicates whether the instrument surface is sterilized or is not sterilized. In various embodiments, surgical tracking server 120 trains models to determine states of various objects identified 510 in video based on states previously determined for an object or for a person from video, allowing the model to determine a state of an object or a person based on characteristics of video including the object or the person. For example, the surgical tracking server 120 applies a label indicating a state of an object or a person to characteristics of video (or other data from sensors) including the object or the person. From the labeled characteristics, the surgical tracking server 120 trains a model using any suitable training method or combination of training methods (e.g., back propagation to train the classification model if it is a neural network, curve fitting techniques if the classification model is a linear regression). The surgical tracking server 120 applies the trained model, or trained models, to characteristics of frames of video data, or to other sensor data, to determine 515 a state of the identified object.

From objects identified 510 within video of the operating room from the image capture devices 110 and states determined 515 for the identified objects, the surgical tracking server 120 determines 520 a phase of the operating room that represents a state of objects within the operating room. The surgical tracking server 120 maintains one or more sets of predefined phases for the operating room in various embodiments. For example, a set of predefined phases includes: a phase indicating the operating room is pre-operative, a phase indicating the operating room is in active surgery, a phase indicating the operating room is post-operative, a phase indicating the operating room is being cleaned, a phase indicating the operating room is idle, and a phase indicating the operating room is available. Different phases of the operating room may include one or more sub-phases to more particularly identify a status of objects within the operating room from captured video of the operating room, as well as data from one or more other types of sensors included in the operating room. For example, a phase indicating the operating room is pre-operative includes a set of sub-phases including a sub-phase indicating a patient is in the operating room, a sub-phase indicating the patient is on a surgical table, a sub-phase indicating the patient is receiving anesthesia, and a sub-phase indicating the patient is draped on the surgical table. In another example, a phase indicating the operating room is in active surgery includes a sub-phase indicating the patient has been opened for surgery, a sub-phase indicating surgical procedures are being performed on the patient, and a sub-phase indicating the patient has been closed. As another example, a phase indicating the operating room is post-operative includes a sub-phase indicating that the patient has been undraped, a sub-phase indicating the patient has woken from anesthesia, a sub-phase indicating the patient has been transferred from the surgical table to a gurney, and a sub-phase indicating the gurney is leaving the operating room. However, the surgical tracking server 120 may maintain any suitable phases, with phases including any suitable number of sub-phases, in various embodiments.

The surgical tracking server 120 accounts for information received from other sensors included in the operating room and coupled to the surgical tracking server 120 when determining 515 states of objects identified in the operating room. For example, the surgical tracking server 120 receives audio from the operating room captured by one or more audio capture devices within the operating room, and one or more models applied to the video from the operating room receive the captured audio as an input for determining 515 states of one or more objects. As another example, the surgical tracking server 120 receives signal strength information from one or more wireless transceivers (e.g., BLU-ETOOTH®) positioned within the operating room and determines locations of client devices within the operating room through triangulation or through any other suitable method; the determined locations of a client devices may be used as a proxy for a locations of objects (e.g., a person) within the operating room and used as input for a trained model determining 515 a state of the object. In another example, an identifier of an object from one or more radio frequency identification (RFID) readers is received by the surgical tracking server 120 and used as an input to a model determining 515 a state of the object. Similarly, temperature or humidity from one or more temperature sensors is received as input to one or more trained models determining 515 states of one or more objects. Hence, the surgical tracking server 120 may use information from various sensors positioned within the operating room to determine 515 a state of one or more objects.

To determine 520 a phase from the obtained video, the surgical tracking server 120 compares positions of identified objects and people in frames and the states determined for the identified objects and people of the obtained video to stored images corresponding to different phases. In various embodiments, the surgical tracking server 120 applies one or more models that determine measures of similarity of frames of the obtained video data to stored images corresponding to phases by comparing positions of identified people and objects in frames of video data to positions of corresponding objects and people in images corresponding to phases and determines 520 a phase of the operating room based on the measures of similarity. An image corresponding to a phase identifies locations within the image of one or more objects in the image and a state corresponding to each of at least a set of identified object. As an example, an image corresponding to a phase identifies locations of different people within the image and identifies whether different people within the image are scrubbed or unscrubbed. In an additional example, an image corresponding to a phase identifies locations of different surfaces within the image and identifies whether different surfaces are sterile or unsterilized. For example, the surgical tracking server 120 determines 520 a phase of the operating room corresponding to a frame of obtained as a phase for which the frame has a maximum measure of similarity. In some embodiments, the surgical tracking server 120 maintains a set of rules associating different phases for the operating room. Each rule includes criteria identifying different locations within frames of video of objects having specific states for a phase, so the surgical tracking server 120 determines 520 a phase of the operating room corresponding to a rule having a maximum number of criteria satisfied by a frame of the obtained video. Alternatively, the surgical tracking server 120 includes a trained phase classification model that receives as inputs states determined for various identified objects and locations of the identified objects within a frame of video and determines a similarity of the combination of identified objects and people and the locations within the frame of the identified objects and people to images corresponding to different phases. The surgical tracking server 120 determines 520 a phase of the operating room as a phase corresponding to an image for which the model determines a maximum similarity. The surgical tracking server 120 may train the phase classification model to determine a likelihood of a combination of states of objects and their locations within a frame of video data matching a phase based on prior matching of combinations of states and locations of objects and people to phases. For example, the surgical tracking server 120 applies a label indicating a phase to a combination of states of objects and locations of the objects in images. From the labeled combinations of states of objects and locations of the objects, the surgical tracking server 120 trains the phase classification model using any suitable training method or combination of training methods (e.g., back propagation to train the classification model if it is a neural network, curve fitting techniques if the classification model is a linear regression). In some embodiments, the surgical tracking server 120 trains different phase classification models corresponding to different phases, maintaining separate phase classification models for different phases. Using a similar sub-phase classification model or rules corresponding to different sub-phases, the surgical tracking server 120 determines a sub-phase of the operating room from video of the operating room, or from data from other sensors within the operating room, when the phase determined 520 for the operating room includes one or more sub-phases. Hence, the surgical tracking server 120 determines both a phase and a sub-phase of the determined phase for the operating room when a phase includes one or more sub-phases.

When determining 520 a phase or a sub-phase of the operating room from video of the operating room, in various embodiments, the surgical tracking server 120 also determines a type of surgery for the operating room. To determine the type of surgery, the surgical tracking server 120 applies one or more surgery classification models that determine measures of similarity of frames of the obtained video data to stored images or videos corresponding to different types of surgery comparing positions of identified people and objects in frames and identified instruments within video to positions of corresponding objects, people, and instruments in images or video corresponding to different types of surgery and determines a type of surgery performed in the operating room based on the measures of similarity. An image or video corresponding to type of surgery identifies locations within the image or within a frame of one or more objects, as well as instruments or positions of instruments, within in the image and a state corresponding to each of at least a set of objects, people, and instruments. As an example, an image or a video corresponding to a type of surgery identifies locations of different people within the image or video, locations of different instruments within the image or video, types of instruments within the image or video. For example, the surgical tracking server 120 determines a type of surgery performed in the operating room corresponding to an image or video of a type of surgery for which the image or video has a maximum measure of similarity. The surgical tracking server 120 may train the surgery classification model to determine a likelihood of video corresponding to a type of surgery based on prior selection of a type of surgery from locations of objects, people, and instruments to the type of surgery. For example, the surgical tracking server 120 applies a label indicating a type of surgery to a combination of people, objects, and instruments in images or video. From the labeled images or video, the surgical tracking server 120 trains the surgery classification model using any suitable training method or combination of training methods (e.g., back propagation to train the classification model if it is a neural network, curve fitting techniques if the classification model is a linear regression). In some embodiments, the surgical tracking server 120 trains different surgery classification models corresponding to different types of surgery, maintaining separate surgery classification models for different types of surgeries. In some embodiments, the surgical tracking server 120 maintains a set of rules associating different types of surgery with the operating room. Each rule includes criteria identifying different locations within frames of video of objects, people, or instruments for a type of surgery, so the surgical tracking server 120 determines a type of surgery performed in the operating room corresponding to a rule having a maximum number of criteria satisfied by the obtained video. In some embodiments, the surgical tracking server 120 determines 520 a phase of the operating room, a sub-phase of the operating room, and a type of surgery for the operating room.

When determining a type of surgery performed in the operating room, the surgical tracking server 120 may also determine a step within the type of surgery from video of the operating room, as well as from other data captured by sensors within the operating room. To determine the step within the type of surgery, the surgical tracking server 120 applies one or more step prediction models, which are trained similarly to the phase classification model, or phase classification models, further described above. For a type of surgery, one or more step prediction models are trained to identify a step within the type of surgery from people, objects, and instruments within the video of the operating room. This allows the surgical tracking server 120 to classify use of the operating room at a high degree of specificity from video or other data from sensors in the operating room without a person in the operating room manually identifying the phase or the step in the type of surgery being performed.

In some embodiments, based on video from an image capture device 110 having a field of view including a door into the operating room, the surgical tracking server 120 determines a number of times the door has opened. In some embodiments, the surgical tracking server 120 identifies the door to the operating room has opened from changes in a position of the door in adjacent frames of video including the door. The surgical tracking server 120 may apply a trained model to frames of video including the door to determine when the door has been opened in some embodiments. In some embodiments, the surgical tracking server 120 determines a number of times the door has opened in different phases of the operating room, allowing the surgical tracking server 120 to maintain a record of a number of times the door has been opened when the operating room is in different phases. The surgical tracking server 120 may also track a number of people who enter and who exit the operating room based on video from the image capture device with a field of view including the door to the operating room. In some embodiments, the surgical tracking server 120 also identifies people who enter and who exit the operating room through facial recognition methods, pose detection methods, or through any other suitable methods, and stores information identifying a person in conjunction with a time when the person entered or exited the operating room. Additionally, the surgical tracking server 120 also identifies a role of a person entering or exiting the operating room based on movement of the person within the operating room or characteristics of the person when entering or exiting the operating room (e.g., whether the person was holding an instrument, an instrument the person was holding, a color of the person's clothing, etc.) and stores the identified role in conjunction with the information identifying the person.

Figure 6:
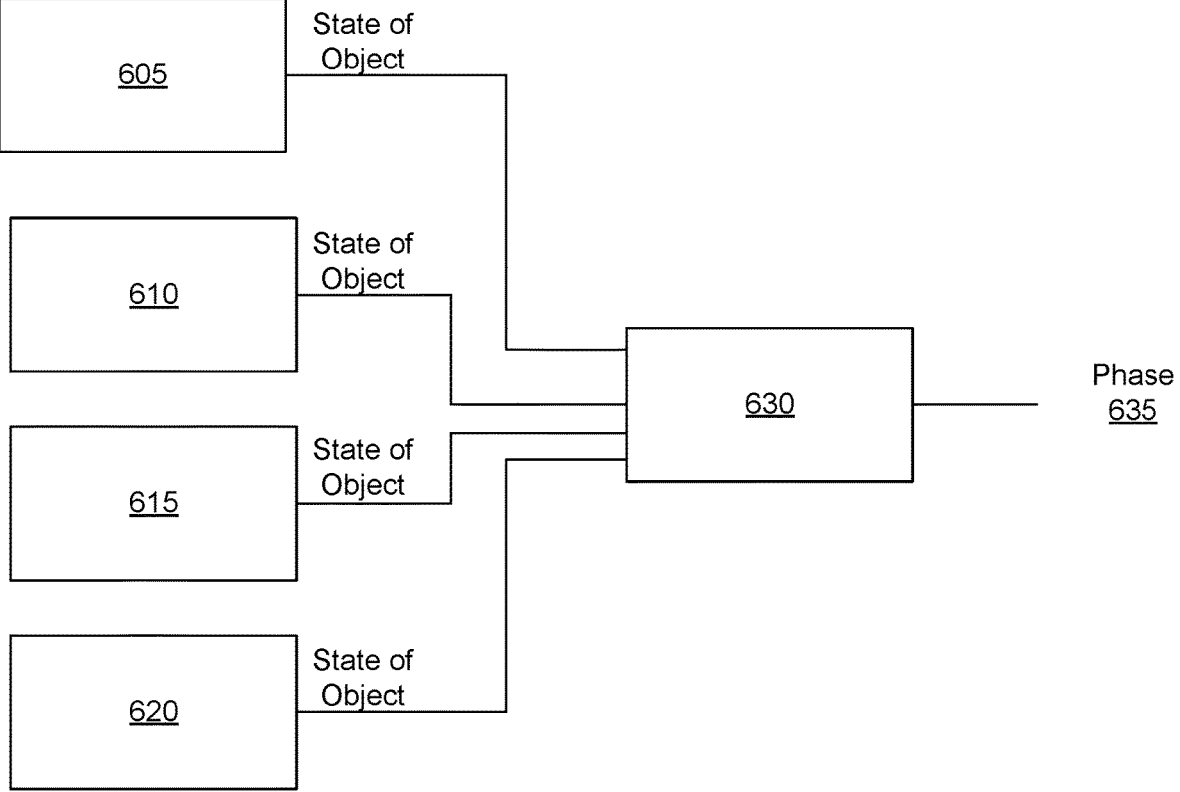
FIG. 6 is a process flow diagram of the surgical tracking server determining a phase of an operating room, in accordance with an embodiment.

FIG. 6 shows a process flow diagram of one embodiment of the surgical tracking server 120 determining a phase of an operating room. In the example shown by FIG. 6, the surgical tracking server 120 applies multiple trained models 605, 610, 615, 620 to video of the operating room from one or more image capture devices 110 that determine a state of various objects identified in the video, as further described above in conjunction with FIG. 5. Hence, each model 605, 610, 615, 620 outputs a state of an object in the video of the operating room. The state of an object output by a model 605, 610, 615, 620 may identify a location of an object within a frame of video or a location of the object relative to one or more other identified objects in various embodiments. In various embodiments, the trained models 605, 610, 615, 620 receive information from other sensors in the operating room, such as audio capture device, wireless transceivers, temperature sensors, or other sensors, and leverage information from the other sensors along with the captured video of the operating room to determine a state of an object in the operating room.

States for various objects in the operating room determined by different trained models 605, 610, 615, 620 are input into a trained phase classification model 630, which determines a phase 635 of the operating room from the combination of states determined for various objects in the operating room. As described above in conjunction with FIG. 5, the phase classification model 630 may be a trained model or may be a set of rules that determine the phase 635 of the operating room from determined states of different objects in the operating room.

Referring back to FIG. 5, the surgical tracking server 120 stores 525 the determined phase in association with the operating room identifier and with a time when the phase was determined 520. From the determined phase, the surgical tracking server 120 or the analytics server 150 generates 530 one or more metrics describing the operating room. For example, a metric determines an amount of time the operating room has been in the determined phase based on prior determinations of the phase of the operating room and time when the prior determinations of the phase of the operating room were performed. The surgical tracking server 120 or the analytics server 150 generates an interface identifying lengths of time that the operating room has been determined 520 to be in different phases in various embodiments. The interface may display information identifying different operating rooms and lengths of time each of the different operating rooms have been in different phases in some embodiments.

Another metric compares the determined amount of time the operating room has been in the determined phase to a desired duration for the determined phase. The desired duration may be specified by a user of the surgical tracking server or may be determined from historical average durations the operating room, or multiple operating rooms, have been in a particular phase. For example, the metric indicates whether the determined amount of time the operating room has been in the determined phase is greater than (or is less than) the desired duration for the determined phase. In another example, the metric indicates an amount of time between the determined amount of time the operating room has been in the determined phase and the desired duration. An additional or alternative metric determines a classification of the determined amount of the time the operating room has been within the determined phase, with different classifications corresponding to different amounts of time; for example, a classification corresponds to an average amount of time in the determined phase, an above average amount of time in the determined phase, and a below average amount of time in the determined phase. Different phases may have different amounts of time corresponding to different classifications in various embodiments. The interface generated by the surgical tracking server 120 or by the analytics server 120 may visually distinguish lengths of time an operating room has been in a phase that exceed a desired duration for the phase or that have a particular classification in some embodiments.

Based on the determined phase or one or more metrics for the operating room, the analytics server 140 (or the surgical tracking server 120) transmits one or more notifications to users. For example, a phase is stored in association with a user, and the analytics server 140 (or the surgical tracking server 120) transmits a notification to the user in response to the determined phase for the operating room matching the phase stored in association with the user. A user may specify different phases for different operating rooms, so the user receives a notification from the analytics server 140 (or the surgical tracking server 120) when a specific operating room is determined to be in a phase specified by the user. The notification may be a push notification, a text message, a multimedia message, an email, or have any other suitable format. A user may specify a format in which the notification is transmitted in some embodiments. For example, the notification is transmitted as a text message or is configured to be displayed by an application associated with the surgical tracking server 120, or with the analytics server 140, that executes on a client device of the user.

Identifying and Evaluating Surgical Time-Out Performance from Captured Video and Audio FIG. 7 is a flowchart of one embodiment of a method for identifying a surgical time-out from captured video of an operating room. In other embodiments, the method includes different or additional steps than those described in conjunction with FIG. 7. Additionally, in some embodiments, steps of the method are performed in a different order than the order described in conjunction with FIG. 7.

A surgical tracking server 120, further described above in conjunction with FIGS. 1 and 3, obtains 705 video of an operating room captured by a plurality of image capture devices 110 positioned within the operating room. As further described above in conjunction with FIGS. 1 and 2, different image capture devices 110 have different positions within an operating room and are positioned to capture video of different locations within the operating room. Each image capture device 110 is configured to communicate with the surgical tracking server 120, which receives video of the operating room captured by each image captured device 110 positioned within the operating room. The image capture devices 110 capture video and audio in various embodiments, and the surgical tracking server 120 obtains 705 the video and audio. In various embodiments, the surgical tracking server 120 obtains an operating room identifier along with the video data, allowing the surgical tracking server 120 identify an operating room for which the video data is obtained 705. In some embodiments, the surgical tracking server 120 receives additional data describing the operating room from other sensors included in the operating room and communicating with the surgical tracking server 120. For example, the surgical tracking server 120 obtains 705 audio from one or more audio capture devices located within the operating room or obtains 705 temperature or humidity data from one or more temperature sensors located in the operating room. Other examples of additional sensors included in the operating room from which the surgical tracking server 120 obtains 505 data include: lidar sensors, wireless transceivers, example, radio frequency identification (RFID), or any other suitable type of sensor.

When performing a surgical procedure in an operating room, personnel involved in the surgical procedure and in the operating room initially perform a "surgical time-out" before beginning the surgical procedure. During the surgical time-out, information about the surgical procedure and the personnel involved in the surgical procedure is audibly presented by personnel in the operating room. In various embodiments, during the surgical time-out, the patient's identity is audibly confirmed, the surgical procedure being performed is audibly identified, a surgical site for the surgical procedure is audibly identified, and identities and roles of personnel involved in the surgical procedure are audibly identified. The surgical tracking server 120 identifies performance of the surgical time out from video and audio obtained 705 from image capture devices or other sensors within the operating room, allowing automatic identification of the surgical time-out.

To identify the surgical time-out, the surgical tracking server 120 retrieves 710 criteria for a surgical time-out. In various embodiments, the surgical tracking server 120 stores the criteria for the surgical time-out, while in other embodiments, the surgical tracking server 120 retrieves 710 the criteria for the surgical time out from another source (e.g., a third party system external to the surgical tracking server 120, an analytics server 140, a remote storage device, etc.). In various embodiments, the criteria for the surgical time-out comprise a library of words or phrases corresponding to initiation of a surgical time-out. In other embodiments, the criteria for the surgical time-out includes poses or positions of people within the operating room corresponding to the surgical time-out, as well as words or phrases.

The surgical tracking server 120 compares 715 video and audio of the operating room to the one or more criteria for the surgical time-out. In response to the comparison determining 720 audio or video satisfy one or more criteria for initiating the surgical time out, the surgical tracking server stores 725 an indication that the surgical time-out was initiated in association with an identifier of the operating room. In some embodiments, an identifier of the surgical procedure being performed in the operating room is also stored in association with the identifier and the identifier of the operating room. The surgical tracking server 120 also stores 730 an indication that video and audio obtained 705 at and after a time when audio or video satisfying the one or more criteria for initiating the surgical time out corresponds to the surgical time-out in association with the obtained video and audio. This allows the surgical tracking server 120 to identify portions of video or audio corresponding to the surgical time-out. In various embodiments, the surgical tracking server 120 applies one or more speech to text models or natural language processing models to audio corresponding to video of the operating room from the one or more image capture devices 110 or from one or more audio capture devices included in the operating room to determine whether the audio includes one or more of the stored words or phrases satisfying one or more criteria for initiating the surgical time-out. Additionally or alternatively, the surgical tracking server 120 obtains one or more criteria specifying specific gestures corresponding to initiation of the surgical time-out and determines whether video from the image capture devices 110 includes gestures matching one or more of the specific gestures corresponding to initiation of the surgical time-out. Hence, based on determining 720 that obtained audio or video satisfies one or more criteria for initiating the surgical time-out, the surgical tracking server 120 stores 725 an indication that the surgical time-out has been initiated with an identifier of the operating room and an identifier of the surgical procedure being performed in the operating room, maintaining a record of initiation of the surgical time-out for different surgical procedures. Additionally, the surgical tracking server 120 stores 730 stores an indication that video or audio received after a time when video or audio of the operating room was determined to satisfy one or more criteria corresponding to initiation of the surgical time-out corresponds to the surgical time-out.

The surgical tracking server 120 also obtains one or more criteria corresponding to ending of the surgical time-out and compares audio and video of the operating room to the one or more criteria corresponding to ending of the surgical time-out. In response to determining audio or video of the operating room satisfies a threshold amount of the one or more criteria corresponding to ending of the surgical time-out, the surgical tracking server 120 stops storing the indication that captured video or audio corresponds to the surgical time-out. In some embodiments, the surgical tracking server 120 stores an ending indicator in association with a time of the audio or video when the audio or video was determined to satisfy the threshold amount of the one or more criteria corresponding to ending of the surgical time out. This allows the surgical tracking server 120 to identify portions of obtained audio or video of the operating room corresponding to a surgical time-out.

From obtained video and audio identified as corresponding to the surgical time-out, the surgical tracking server 120 or an analytics server 140, further described above in conjunction with FIG. 4, generates 735 one or more quality metrics describing the surgical time-out by applying one or more trained models to audio and video identified as corresponding to the surgical time-out and to stored quality criteria for the surgical time-out. In various embodiments, the surgical tracking server 120 or the analytics serer 140 maintains a set of quality criteria for a surgical time-out, with different quality criteria identifying different information expected to be provided during the surgical time-out. Example quality criteria include audible identification of each person in the operating room participating in the surgical procedure and their role in a surgical procedure, audible identification of a patient's identity, audible identification of the surgical procedure to be performed, audible identification of a surgical site on which the surgical procedure is to be performed, audible identification of patient-specific concerns for anesthesia, audible identification of sterility of instruments to be used in the surgical procedure, audible identification of one or more steps in the surgical procedure (or other information describing the surgical procedure), and any other suitable information describing the surgical procedure. In various embodiments, different quality criteria include different words or phrases corresponding to different information. For example, various quality criteria include names or descriptions of surgical procedures and names or descriptions of instruments. The surgical tracking server 120 or the analytics server 140 applies one or more trained models to audio and video identified as corresponding to the surgical time-out to compare the portions of audio and video identified as corresponding to the surgical time-out to the stored set of quality criteria for the surgical time-out, and generates a completion metric indicating completion of the surgical time-out in response to content from the audio and video identified as corresponding to the surgical time-out satisfying at least a threshold amount of the stored set of quality criteria. In some embodiments, the completion metric is a binary value that indicates whether or not the audio and video corresponding to the surgical time out satisfied the threshold amount of the stored set of quality metrics, while in other embodiments the completion metric is a score based on an amount of the quality criteria satisfied by the audio and video corresponding to the surgical time out. To determine the completion metrics, in various embodiments the analytics server 140 or the surgical tracking server 120 applies one or more speech to text methods or natural language processing methods to audio and video identified as corresponding to the surgical time-out to extract content from the audio and video identified as corresponding to the surgical time-out for comparison to the set of criteria.

In some embodiments, to determine whether each person in the operating room participating in the surgical procedure identifies themselves and their roles in the surgical procedure, the surgical tracking server 120 or the analytics server 140 identifies regions of video of the operating room corresponding to each person participating in the surgical procedure through any suitable computer vision method or combination of computer vision methods. The surgical tracking server 120 or the analytics server 140 determines a region of the video corresponding to a person speaking for different audio during the audio and video identified as corresponding to the surgical time-out by application of one or more trained classification models to the video data. For each person identified as speaking, the surgical tracking server 120 or the analytics server 140 determines whether portions of audio from an identified person matches stored information identifying names and matching roles in a surgical procedure. The surgical tracking server 120 or the analytics server 140 stores a flag in association with each identified person that indicates whether portions of audio from an identified person matches stored information identifying names and matching roles in a surgical procedure. In response to the flag stored in association with each identified person indicating that portions of audio from portions of audio from the identified person matches stored information identifying names and matching roles in a surgical procedure, the surgical tracking server 120 or the analytics server 140 determines that each identified person has identified themselves and their role in the surgical procedure.

The surgical tracking server 120 or the analytics server 140 may determine the quality metrics in near real-time in various embodiments and determine one or more of the quality metrics when video and audio indicated as corresponding to the surgical time-out is received. This allows the surgical tracking server 120 or the analytics server 140 to provide notifications to people in the operating room based on the quality metrics describing performance of the surgical time-out. In some embodiments, the surgical tracking server 120 or the analytics server 140 transmits a notification to a display in the operating room, with the notification displaying a message, symbol, or other information in response to the surgical tracking server 120 or the analytics server 140 determining that each identified person has identified themselves and their role in the surgical procedure; in some embodiments, an alternative notification is transmitted to the display to indicate that one or more identified people have not identified themselves or their role in the surgical procedure.

In some embodiments, one or more quality metrics for the surgical time-out evaluates attentiveness of identified people in the video of the operating room during portions of video identified as corresponding to the surgical time-out. For example, the surgical tracking server 120 or the analytics server 140 determines an ambient noise level during the video and audio corresponding to the surgical time-out from the captured video and audio corresponding to the surgical time-out; a quality metric generated by the surgical tracking server 120 or the analytics server 140 indicates whether the determined ambient noise level exceeds a threshold or identifies a range of ambient noise levels including the determined ambient noise level. Based on comparison of the determined ambient noise level to the threshold or to a range, the surgical tracking server 120 or the analytics server 140 generates a quality metric identifying whether the determined ambient noise exceeded a threshold indicating an ambient noise level over which audio comprising the surgical time-out is likely to have been audible to the people in the operating room. In another example, the surgical tracking server 120 or the analytics server 140 determines an amount of motion by identified people in the portion of the video data corresponding to the surgical time-out, and generates a value quantifying the amount of motion. By comparing the value quantifying the amount of motion by identified people in the operating room, the surgical tracking server 120 or the analytics server 140 generates a quality metric representing a level of attentiveness of identified people in the operating room during the surgical time-out, with a lower value of the quality metric corresponding to greater amounts of motion and a higher value of the quality metric corresponding to lower amounts of motion. In some embodiments, the surgical tracking server 120 or the analytics server 140 generates an indication whether the quality metric representing a level of attentiveness equals or exceeds a threshold value. Hence, the surgical tracking server 120 or the analytics server 140 may use an amount of motion by identified people in the operating room as a proxy for a level of attentiveness by the identified people in the operating room during the surgical timeout. As another example, a quality metric identifies a number of identified people moving in and out of a region of the operating room, such as a region within a threshold distance of a surgical table or the operating room, by tracking different identified people in the obtained video corresponding to the surgical time-out. In some embodiments, the surgical tracking server 120 or the analytics server 140 maintains time-out quality model that generates an overall quality metric for a surgical time-out from a combination of the previously described metrics, as well as any other suitable metrics determined from audio or video corresponding to the surgical time-out.

In some embodiments, the surgical tracking server 120 or the analytics server 140 accounts for a determined phase or sub-phase of the operating room, as further described above in conjunction with FIGS. 5 and 6, to generate and to transmit one or more notifications to users about the surgical time-out. For example, the surgical tracking server 120 or the analytics server 140 stores a specific phase or sub-phase of the operating room during which the surgical time-out is performed. In response to determining a phase, or sub-phase, of the operating room is subsequent to the phase or the sub phase during which the surgical time-out is performed and to determining no obtained video or audio data from has a stored indication of corresponding to the surgical time-out, the surgical tracking server 120 or the analytics server 140 transmits a notification to one or more displays in the operating room displaying a prompt or a message to perform the surgical time-out. In other embodiments, the surgical tracking server 120 or the analytics server 140 maintains a predicted duration of a sub-phase or a phase in which the surgical time-out is performed based on durations of the sub-phase or phase from prior surgeries. In response to determining an operating room has been in the sub-phase or phase in which the surgical time-out is performed for a length of time that is within a threshold amount of time from the predicted duration of the sub-phase or phase and determining that no obtained video or audio has a stored indication of corresponding to the surgical time-out, the surgical tracking server 120 or the analytics server 140 transmits a notification to one or more displays in the operating room displaying a prompt or a message to perform the surgical time-out.

Figure 8:
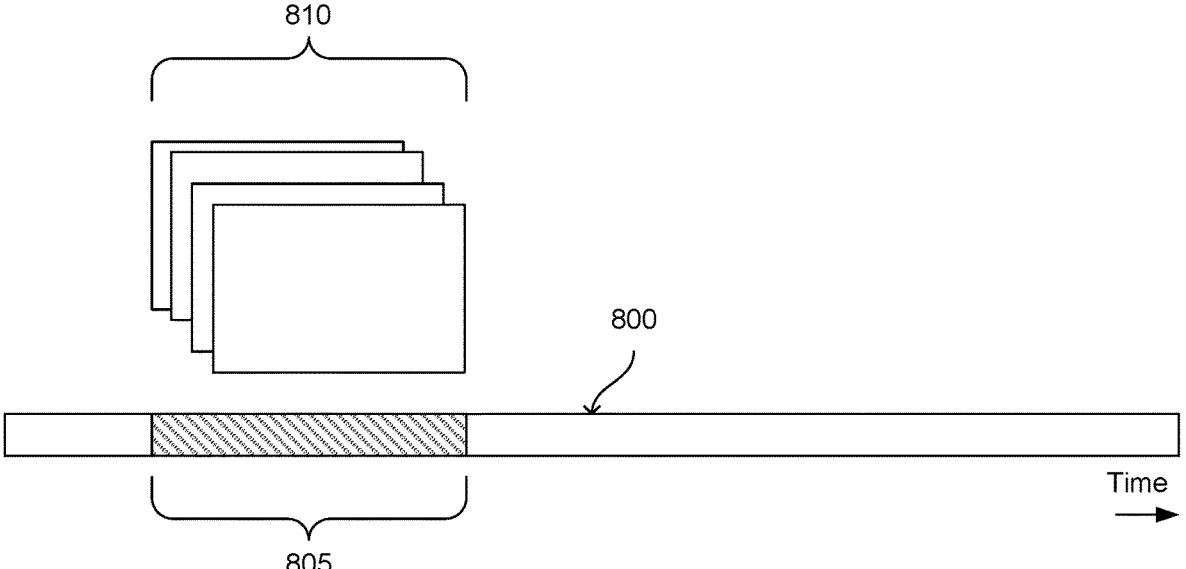
FIG. 8 is an example showing identification of a surgical time-out from captured audio and video of an operating room, in accordance with an embodiment.

FIG. 8 is an example showing identification of a surgical time-out from captured audio and video of an operating room. In FIG. 8, a timeline 800 represents audio and video captured of an operating room at different times, such as at different times during a surgical procedure performed in the operating room. As further described above in conjunction with FIG. 7, a surgical tracking server compares audio and video to one or more criteria for a surgical time-out. In the example of FIG. 8, time interval 805 includes audio and video 810 of the operating room associated with an indication that the surgical time out was initiated. For example, time interval 805 includes audio and video capture from a time when the surgical tracking server 120 determined audio and video of the operating room satisfied one or more criteria corresponding to initiating the surgical time-out to a time when the surgical tracking server 120 determined audio and video of the operating room satisfied one or more criteria corresponding to ending the surgical time-out. As further described above in conjunction with FIG. 7, the surgical tracking server 120, or an analytics server 140 coupled to the surgical tracking server 120, generates one or more quality metrics for the surgical time-out by applying one or more models to the audio and video 810 of the operating room associated with the indication the surgical time-out was initiated to generate one or more quality metrics for the surgical time-out based on a set of quality criteria. Hence, the surgical tracking server 120 identifies when a surgical time-out occurs through application of one or more models to audio and video of the operating room and generates one or more quality metrics describing performance of the surgical time-out by application of additional trained models to evaluate the audio and video 810 associated with the indication the surgical time-out was initiated against a set of quality criteria.

Additional Configuration Considerations

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments of the invention may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments of the invention may also relate to a product that is produced by a computing process described herein. Such a product may comprise information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

What is claimed is:

1. A method comprising:

obtaining video of an operating room from a plurality of image capture devices positioned within the operating room, different image capture devices having different locations within the operating room;

obtaining audio of the operating room;

comparing, through application of one or more models by a surgical tracking server, the audio and video of the operating room to one or more criteria corresponding to performance of a surgical time-out; and in response to determining that the obtained audio and video of the operating room satisfy one or more criteria corresponding to initiating the surgical time-out, storing an indication that the surgical time-out has been initiated with an identifier of the operating room;

generating a quality metric indicating completion of the surgical time-out in response to audio and video data of the operating room collected after the surgical time-out has been initiated satisfying a threshold amount of quality criteria, wherein the quality metric is generated by applying one or more trained models to the audio and video data of the operating room collected after the surgical time-out has been initiated and the quality criteria; and storing an indication of the completion of the surgical time-out in association with the audio and video of the operating room collected after the surgical time-out has been initiated.

2. The method of claim 1, wherein the one or more obtained criteria correspond to initiating the surgical time-out, the one or more obtained criteria comprising a stored word or a stored phrase.

3. The method of claim 2, wherein comparing, through application of one or more models, the audio and video of the operating room to the one or more criteria corresponding to performance of the surgical time-out comprises:

determining whether audio of the operating room includes the stored word or the stored phrase.

4. The method of claim 1, wherein the quality criteria comprise one or more criteria corresponding to the completion of the surgical time-out, the method further comprising:

comparing audio and video of the operating room collected after the surgical time-out has been initiated to one or more criteria corresponding to the completion of the surgical time-out;

in response to the comparing of the audio and video of the operating room collected after the surgical time-out has been initiated to one or more criteria corresponding to the completion of the surgical time-out, determining the audio and video of the operating room collected after the surgical time-out has been initiated satisfy the one or more criteria corresponding to the completion of the surgical time-out; and stopping storing the indication of the completion of the surgical time-out.

5. The method of claim 4, further comprising:

storing an ending indicator in association with the time when the audio and video of the operating room collected after the surgical time-out has been initiated were determined to satisfy the one or more criteria corresponding to the completion of the surgical time-out.

6. The method of claim 1, wherein generating a quality metric indicating completion of the surgical time-out comprises:

generating a completion metric indicating completion of the surgical time-out in response to content from the audio and video of the operating room collected after the surgical time-out has been initiated satisfying at least a threshold amount of quality criteria.

7. The method of claim 1, wherein the quality criteria comprises one or more of the following: audible identification of each person in the operating room participating in a surgical procedure and their role in the surgical procedure, audible identification of a patient's identity, audible identification of the surgical procedure to be performed, audible identification of a surgical site on which the surgical procedure is to be performed, audible identification of patient-specific concerns for anesthesia, audible identification of sterility of instruments to be used in the surgical procedure, audible identification of one or more steps in the surgical procedure, and any combination thereof.

8. The method of claim 6, wherein the completion metric comprises a score based on an amount of quality criteria satisfied by the audio and video of the operating room collected after the surgical time-out has been initiated.

9. The method of claim 1, wherein generating a quality metric indicating completion of the surgical time-out comprises:

determining an ambient noise level in the operating room during the audio and video of the operating room collected after the surgical time-out has been initiated; and generating a quality metric indicating whether the ambient noise level exceeded a threshold.

10. The method of claim 1, wherein generating a quality metric indicating completion of the surgical time-out comprises:

determining a number of people moving in and out of a region of the operating room identified in video of the operating room collected after the surgical time-out has been initiated.

11. The method of claim 1, further comprising:

transmitting a notification to a display in the operating room based on the quality metric.

12. The method of claim 11, wherein transmitting the notification to the display in the operating room based on the quality metric comprises:

transmitting the notification to the display in the operating room in response to determining that each identified person in the audio and video of the operating room has identified themselves and their role in a surgical procedure.

13. The method of claim 11, wherein transmitting the notification to the display in the operating room based on the one or more quality metrics comprises:

transmitting the notification to the display in the operating room in response to determining that at least one person in the audio and video of the operating room collected after the surgical time-out has been initiated has not identified themselves or their role in a surgical procedure.

14. The method of claim 1, further comprising:

determining a sub-phase of the operating room from the audio and video of the operating room collected after the surgical time-out has been initiated;

retrieving a specific sub-phase of the operating room during which the surgical time-out is to be performed; and in response to the determined sub-phase of the operating room being a sub-phase that is later than the specific sub-phase and in response to the indication that the surgical time-out has been initiated not being stored, transmitting a notification to a display included in the operating room including a prompt to perform the surgical time-out.

15. The method of claim 1, further comprising:

determining a sub-phase of the operating room from the audio and video of the operating room collected after the surgical time-out has been initiated;

retrieving a specific sub-phase of the operating room during which the surgical time-out is to be performed;

retrieving a predicted duration for the specific sub-phase; and in response to a length of time the operating room has been in the determined sub-phase of the operating room being within a threshold amount of time from the predicted time and in response to the indication that the surgical time-out has been initiated not being stored, transmitting a notification to a display included in the operating room including a prompt to perform the surgical time-out.

16. A computer program product comprising a non-transitory computer readable storage medium having instructions encoded thereon that, when executed by a processor, cause the processor to:

obtain video of an operating room from a plurality of image capture devices positioned within the operating room, different image capture devices having different locations within the operating room;

obtain audio of the operating room;

compare, through application of one or more models by a surgical tracking server, the audio and video of the operating room to one or more criteria corresponding to performance of a surgical time-out; and in response to determining that the obtained audio and video of the operating room satisfy one or more criteria corresponding to initiating the surgical time-out, store an indication that the surgical time-out has been initiated with an identifier of the operating room;

generate a quality metric indicating completion of the surgical time-out in response to audio and video data of the operating room collected after the surgical time-out has been initiated satisfying a threshold amount of quality criteria, wherein the quality metric is generated by applying one or more trained models to the audio and video data of the operating room collected after the surgical time-out has been initiated and the quality criteria; and store an indication of the surgical time-out in association with subsequently received audio and video of the operating room obtained after a time when the audio and video of the operating room were determined to satisfy the one or more criteria corresponding to initiating the surgical time-out.

17. The computer program product of claim 16, wherein the one or more obtained criteria correspond to initiating the surgical time-out, the one or more obtained criteria comprising a stored word or a stored phrase.

18. The computer program product of claim 17, wherein compare, through application of one or more models, the audio and video of the operating room to the one or more criteria corresponding to performance of the surgical time-out comprises:

determine whether audio of the operating room includes the stored word or the stored phrase.

19. The computer program product of claim 16, wherein the quality criteria comprise one or more criteria corresponding to the completion of the surgical time-out, wherein the non-transitory computer readable storage medium further has instructions encoded thereon that, when executed by the processor, further cause the processor to:

compare audio and video of the operating room collected after the surgical time-out has been initiated to one or more criteria corresponding to the completion of the surgical time-out;

in response to the comparing of the audio and video of the operating room collected after the surgical time-out has been initiated to one or more criteria corresponding to the completion of the surgical time-out, determine the audio and video of the operating room collected after the surgical time-out has been initiated satisfy the one or more criteria corresponding to the completion of the surgical time-out; and stop storing the indication of the completion of the surgical time-out.

20. The computer program product of claim 19, wherein the non-transitory computer readable storage medium further has instructions encoded thereon that, when executed by the processor, cause the processor to:

store an ending indicator in association with the time when the audio and video of the operating room collected after the surgical time-out has been initiated were determined to satisfy the one or more criteria corresponding to the completion of the surgical time-out.

21. The computer program product of claim 16, wherein instructions to generate a quality metric indicating completion of the surgical time-out further comprises instructions that cause the processor to:

generate a completion metric indicating completion of the surgical time-out in response to content from the audio and video of the operating room collected after the surgical time-out has been initiated satisfying at least a threshold amount of quality criteria.

22. The computer program product of claim 21, wherein the completion metric comprises a score based on an amount of quality criteria satisfied by the audio and video of the operating room collected after the surgical time-out has been initiated.

23. The computer program product of claim 16, wherein the quality criteria comprises one or more of the following: audible identification of each person in the operating room participating in a surgical procedure and their role in the surgical procedure, audible identification of a patient's identity, audible identification of the surgical procedure to be performed, audible identification of a surgical site on which the surgical procedure is to be performed, audible identification of patient-specific concerns for anesthesia, audible identification of sterility of instruments to be used in the surgical procedure, audible identification of one or more steps in the surgical procedure, and any combination thereof.

24. The computer program product of claim 16, wherein instructions to generate a quality metric indicating completion of the surgical time-out further comprises instructions that cause the processor to:

determine an ambient noise level in the operating room during the audio and video of the operating room collected after the surgical time-out has been initiated; and generate a quality metric indicating whether the ambient noise level exceeded a threshold.

25. The computer program product of claim 16, wherein instructions to generate a quality metric indicating completion of the surgical time-out further comprises instructions that cause the processor to:

determine a number of people moving in and out of a region of the operating room identified in video of the operating room collected after the surgical time-out has been initiated.

26. The computer program product of claim 16, wherein the non-transitory computer readable storage medium further has instructions encoded thereon that, when executed by the processor, cause the processor to:

transmit a notification to a display in the operating room based on the quality metric.

27. The computer program product of claim 26, wherein instructions to transmit the notification to the display in the operating room based on the one or more quality metrics further comprises instructions that cause the processor to:

transmit the notification to the display in the operating room in response to determining that each identified person in the audio and video of the operating room has identified themselves and their role in a surgical procedure.

28. The computer program product of claim 26, wherein instructions to transmit the notification to the display in the operating room based on the one or more quality metrics further comprises instructions that cause the processor to:

transmit the notification to the display in the operating room in response to determining that at least one person in the audio and video of the operating room collected after the surgical time-out has been initiated has not identified themselves or their role in a surgical procedure.

29. The computer program product of claim 16, wherein the non-transitory computer readable storage medium further has instructions encoded thereon, that when executed by the processor, cause the processor to:

determine a sub-phase of the operating room from the audio and video of the operating room collected after the surgical time-out has been initiated;

retrieve a specific sub-phase of the operating room during which the surgical time-out is to be performed; and in response to the determined sub-phase of the operating room being a sub-phase that is later than the specific sub-phase and in response to the indication that the surgical time-out has been initiated not being stored, transmit a notification to a display included in the operating room including a prompt to perform the surgical time-out.

30. The computer program product of claim 16, wherein the non-transitory computer readable storage medium further has instructions encoded thereon, that when executed by the processor, cause the processor to:

determine a sub-phase of the operating room from the audio and video of the operating room collected after the surgical time-out has been initiated;

retrieve a specific sub-phase of the operating room during which the surgical time-out is to be performed;

retrieve a predicted duration for the specific sub-phase; and in response to a length of time the operating room has been in the determined sub-phase of the operating room being within a threshold amount of time from the predicted time and in response to the indication that the surgical time-out has been initiated not being stored, transmit a notification to a display included in the operating room including a prompt to perform the surgical time-out.

* * * * *